US006096502A

United States Patent [19]
Lee

[11] Patent Number: 6,096,502
[45] Date of Patent: Aug. 1, 2000

[54] SUBSTRATE FOR DETECTING UL9 HELICASE ACTIVITY

[75] Inventor: Sam S.-K. Lee, 601 Almarida Dr., T-11, Campbell, Calif. 95008

[73] Assignee: Sam S.-K. Lee, Bothwell, Wash.

[21] Appl. No.: 09/050,559

[22] Filed: Mar. 30, 1998

[51] Int. Cl.[7] .............................. C12Q 1/68; C12Q 1/70; C07H 19/00; C07H 21/02

[52] U.S. Cl. .................................. 435/6; 435/5; 435/7.1; 436/501; 436/504; 536/22.1; 536/23.1; 935/77; 935/82

[58] Field of Search .................... 435/6, 5, 7.1; 436/501, 436/504; 536/22.1, 23.1; 935/77, 82

[56] References Cited

PUBLICATIONS

Fierer, D. et al., "The Stoichiometry of Binding of the Herpes Simplex Virus Type Origin Binding Protein, UL9, to Ori$_s$", *The Journal of Biological Chemistry*, vol. 270, No. 13, Mar. 31, 1995, pp. 7330–7334.

Boehmer, P. et al., "Association of Origin Binding Protein and Single Strand DNA–binding Protein, ICP8, during Herpes Simplex Virus Type 1 DNA Replication in Vivo", *The Journal of Biological Chemistry*, vol. 269, No. 46, Nov. 18, 1994, pp. 29329–29334.

Lee, Sam S.-K. et al., "Unwinding of the box I element of a herpes simplex virus type 1 origin by a complex of the viral origin binding protein, single–strand DNA binding protein, and single–stranded DNA", *Proc. Natl. Acad. Sci. USA*, vol. 94, pp. 2838–2842, Apr. 1997.

Weir, H. et al., "Binding of the herpes simplex virus type 1 UL9 gene product to an origin of viral DNA replication", *Nucleic Acids Research*, vol. 17, No. 4, (1989), pp. 1429–1425.

Gustafsson, C. et al., "The DNA Ligands Influence the Interactions between the Herpes Simplex Virus 1 Origin Binding Protein and the Single Strand DNA–binding Protein, ICP–8", *The Journal of Biological Chemistry*, vol. 270, No. 32, Aug. 11, 1995, pp. 19028–19034.

Elias, P. et al., "Structural Elements Required for the Cooperative Binding of the Herpes Simplex Virus Origin Binding Protein to oriS Reside in the N–Terminal Part of the Protein", *The Journal of Biological Chemistry*, vol. 267, No. 24, Aug. 25, 1992, pp. 17424–17429.

Stabell, E. et al., "A truncated herpes simplex virus origin binding protein which contains the carboxyl terminal origin binding domain binds to the origin of replication but does not alter its conformation", *Nucleic Acids Research*, vol. 21, No. 22, (1993), pp. 5203–5211.

Elias, P. et al., "The Origin Binding Protein of Herpes Simplex Virus 1 Binds Cooperatively to the Viral Origin of Replication Ori$_s$", *The Journal of Biological Chemistry*, vol. 265, No. 28, Oct. 5, 1990, pp. 17167–17173.

Olivo, P. et al., "Herpes simplex virus DNA replication: The UL9 gene encodes an origin–binding protein", *Proc. Natl. Acad. Sci. USA*, vol. 85, pp. 5414–5418, Aug. 1988.

Weir, H. et al., "Two binding sites for the herpes simplex virus type 1 UL9 protein are required for efficient activity of the ori$_s$ replication origin", *Journal of General Virology* (1990), vol. 71, pp. 1379–1385.

Hazuda, D. et al., "Cooperative Interactions between Replication Origin–bound Molecules of Herpes Simplex Virus Origin–binding Protein Are Mediated via the Amino Terminus of the Protein", *The Journal of Biological Chemistry*, vol. 267, No. 20, Jul. 15, 1992, pp. 14309–14315.

Elias, P. et al., "A DNA binding protein specific for an origin of replication of herpes simples virus type 1", *Proc. Natl. Acad. Sci. USA*, vol. 83, pp. 6322–6326, Sep. 1986.

Earnshaw, D. et al., "Characterisation of the Nucleotide and DNA Coeffictor Binding Sites of the Herpes Simplex Virus Type 1 (HSV–1) Encoded Helicase–Primase Complex and UL9 Origin Binding Protein", *Biochemical and Biophysical Research Communications*, vol. 199, No. 3, Mar. 30, 1994, pp. 1333–1340.

Koff, A. et al., "Herpes Simplex Virus Origin–Binding Protein (UL9) Loops and Distorts the Viral Replication Origin", *Journal of Virology*, vol. 65, No. 6, Jun. 1991, pp. 3284–3292.

Gustafsson, C. et al., "Herpes simplex virus DNA replication: A spacer sequence directs the ATP–dependent formation of a nucleoprotein complex at ori$_s$", *Proc. Natl. Acad. Sci. USA*, vol. 91, pp. 4629–4633, May 1994.

Hazuda, D. et al., "Characterization of Herpes Simplex Virus Origin Binding Protein Interaction with Ori$_s$", *The Journal of Biological Chemistry*, vol. 266, No. 36, Dec. 25, 1991, pp. 24621–24626.

Koff, A. et al., "Characterization of Major Recognition Sequences for Herpes Simplex Virus Type 1 Origin–Binding Protein", *Journal of Virology*, vol. 62, No. 11, Nov. 1988, pp. 4096–4103.

(List continued on next page.)

*Primary Examiner*—Mary E. Mosher
*Assistant Examiner*—Ali R. Salimi
*Attorney, Agent, or Firm*—David J. Weitz; Wilson Sonswi Goodrich & Rosati

[57] ABSTRACT

A UL9 substrate for detecting helicase activity in a UL9 protein is provided. In one embodiment, the substrate includes a first strand including a herpes replication origin sequence and a first single stranded tail; and a second strand including a sequence complementary to the herpes replication origin sequence. In one variation, the first single stranded tail is 3' relative to the herpes replication origin sequence. The second strand may optionally further include a single stranded tail. The single stranded tail on the second strand may be 3' or 5' relative to the sequence complementary to the herpes replication origin sequence. In another variation, the first single stranded tail is 5' relative to the herpes replication origin sequence. The second strand may optionally further include a single stranded tail. The single stranded tail on the second strand may be 3' or 5' relative to the sequence complementary to the herpes replication origin sequence. The UL9 substrate may optionally further include at least one detectable marker attached to at least one of the first and second strands. The UL9 substrate may also optionally be attached to a solid support.

45 Claims, 17 Drawing Sheets

OTHER PUBLICATIONS

Hammarsten, O. et al., "Characterization of a binding site for the herpes simplex virus type 1 UL9 origin–binding protein within the UL9 gene", *Journal of General Virology*, vol. 77, pp. 969–976, (1996).

Martin, D.W. et al., "Analysis of the DNA–Binding Domain of the HSV–1 Origin–Binding Protein", *Virology*, vol. 198, pp. 71–80, 1994.

Arbuckle, M. et al., "A mutational analysis of the DNA–binding domain of the herpes simplex virus type 1 UL9 protein", *Journal of General Virology*, vol. 74, pp. 1349–1355, (1993).

Stow, N., "Herpes simplex virus type 1 origin–dependent DNA replication in insect cells using recombinant baculoviruses", *Journal of General Virology*, vol. 73, pp. 313–321, (1992).

Wu, C. et al., "Identification of Herpes Simplex Virus Type 1 Genes Required for Origin–Dependent DNA Synthesis", *Journal of Virology*, vol. 62, No. 2, Feb. 1988, pp. 435–443.

Challberg, M., "A Method for identifying the viral genes required for herpesvirus DNA replication", *Proc. Natl. Acad. Sci. USA*, vol. 83, pp. 9094–9098, Dec. 1986.

Martinez, R. et al., "The Conserved Helicase Motifs of the Herpes Simplex Virus Type 1 Origin–Binding Protein UL9 Are Important for Function", *Journal of Virology*, vol. 66, No. 11, Nov. 1992, pp. 6735–6746.

Chen, D. et al., "Varicella–Zoster Virus Gene 51 Complements a Herpes Simplex Virus Type 1 UL9 Null Mutant", *Journal of Virology*, vol. 69, No. 7, Jul. 1995, pp. 4515–4518.

Inoue, N. et al., "Human Herpesvirus 6B Origin–Binding Protein: DNA–Binding Domain and Consensus Binding Sequence", *Journal of Virology*, vol. 69, No. 8, Aug. 1995, pp. 4619–4627.

Inoue, N. et al., "Alphaherpesvirus Origin–Binding Protein Homolog Encoded by Human Herpesvirus 6B, a Betaherpesvirus, Binds to Nucleotide Sequences That Are Similar to ori Regions of Alphaherpesviruses", *Journal of Virology*, vol. 68, No. 7, Jul. 1994, pp. 4126–4136.

Chen, D. et al., "Expression of the Varicella–Zoster Virus Origin–Binding Protein and Analysis of Its Site–Specific DNA–Binding Properties", *Journal of Virology*, vol. 68, No. 6, Jun. 1994, pp. 3841–3849.

Martin, D. et al., "Analysis of the Herpes Simplex Virus Type 1 $Ori_s$ Sequence: Mapping of Functional Domains", *Journal of Virology*, vol. 65, No. 8, Aug. 1991, pp. 4359–4369.

Lockshon, D. et al., "Sequence and Structural Requirements of a Herpes Simplex Viral DNA Replication Origin", *Molecular and Cellular Biology*, vol. 8, No. 10, Oct. 1988, pp. 4018–4027.

Hardwicke, M. et al., "Cloning and Characterization of Herpes Simplex Virus Type 1 oriL: Comparison of Replication and Protein–DNA Complex Formation by oriL and oriS", *Journal of Virology*, vol. 69, No. 3, Mar. 1995, pp. 1377–1388.

Wong, S. et al., "Elements in the Transcriptional Regulatory Region Flanking Herpes Simplex Virus Type 1 oriS Stimulate Origin Function", *Journal of Virology*, vol. 65, No. 5, May 1991, pp. 2601–2611.

Deb, S. et al., "A 67–Base–Pair Segment from the Ori–S Region of Herpes Simplex Virus Type 1 Encodes Origin Function", *Journal of Virology*, vol. 62, No. 7, pp. 2516–2519.

Klupp, B. et al., "The Virulence–Determining Genomic BamHI Fragment 4 of Pseudorabies Virus Contains Genes Corresponding to the $U_l15$ (Partial), $U_L18$, $U_L19$, $U_L20$ and $U_L21$ Genes of Herpes Simplex Virus and a Putative Origin of Replication", *Virology*, vol. 191, pp. 900–908, (1992).

Baumann, R. et al., "Functional Mapping and DNA Sequence of an Equine Herpesvirus 1 Origin of Replication", *Journal of Virology*, vol. 63, No. 3, Mar. 1989, pp. 1275–1283.

van Loon, N. et al., "Identification and Analysis of a Lytic–Phase Origin of DNA Replication in Human Herpesvirus 7", *Journal of Virology*, vol. 71, No. 4, Apr. 1997, pp. 3279–3284.

Dewhurst, S. et al., "Identification of a Lytic–Phase Origin of DNA Replication in Human Herpesvirus 6B Strain Z29", *Journal of Virology*, vol. 67, No. 12, Dec. 1993, pp. 7680–7683.

Dewhurst, S. et al., "Human Herpesvirus 6B Origin: Sequence Diversity, Requirement for Two Binding Sites for Origin–Binding Protein, and Enhanced Replication from Origin Multimers", *Journal of Virology*, vol. 68, No. 10, Oct. 1994, pp. 6799–6803.

Olivo, P. et al., "Herpes Simplex Virus Type 1 Gene Products Required for DNA Replication: Identification and Overexpression", *Journal of Virology*, vol. 63, No. 1, Jan. 1989, pp. 196–204.

Kinchington, P. et al., "Identification and Characterization of a Varicella–Zoster Virus DNA Binding Protein by Using Antisera Directed against a Predicted Synthetic Oligopeptide", *Journal of Virology*, vol. 62, No. 3, Mar. 1988, pp. 802–809.

Ruyechan, W. et al., "Surface Lysine and Tyrosine Residues Are Required for Interaction of the Major Herpes Simplex Virus Type 1 DNA–Binding Protein with Single–Stranded DNA", *Journal of Virology*, vol. 66, No. 11, Nov. 1992, pp. 6273–6279.

Wang, Y. et al., "Characterization of a Major DNA–Binding Domain in the Herpes Simplex Virus Type 1 DNA–Binding Protein (ICP8)", *Journal of Virology*, vol. 64, No. 5, May 1990, pp. 2082–2089.

Ruyechan, W. et al., "Interaction with Nucleic Acids and Stimulation of the Viral DNA Polymerase by the Herpes Simplex Virus Type 1 Major DNA–Binding Protein", *Journal of Virology*, vol. 52, No. 3, Dec. 1984, pp. 727–733.

Lee, C. et al., "An Immunoassay for the Study of DNA–Binding Activities of Herpes Simplex Virus Protein ICP8", *Journal of Virology*, vol. 54, No. 3, Jun. 1985, pp. 731–738.

Ruyechan, W., "The Major Herpes Simplex Virus DNA–Binding Protein Holds Single–Stranded DNA in an Extended Configuration", *Journal of Virology*, vol. 46, No. 2, May 1983, pp. 661–666.

Dutch, R. et al., "Renaturation of Complementary DNA Strands by Herpes Simplex Virus Type 1 ICP8", *Journal of Virology*, vol. 67, No. 12, Dec. 1993, pp. 6945–6949.

Boehmer, P. et al., "Herpes Simplex Virus Type 1 ICP8: Helix–Destabilizing Properties", *Journal of Virology*, vol. 67, No. 2, Feb. 1993, pp. 711–715.

Gao, M. et al., "Genetic Identification of a Portion of the Herpes Simplex Virus ICP8 Protein Required for DNA–Binding", *Virology*, vol. 163, pp. 319–329, (1988).

Leinbach, S. et al., "Characterization of the single–stranded DNA–binding domain of the herpes simplex virus protein ICP8", *Biochimica et Biophysica Acta.*, vol. 1008, pp. 281–286, (1989).

Bayliss, G. et al., "Herpes Simplex Virus Proteins: DNA–Binding Proteins in Infected Cells and in the Virus Structure", *Virology*, vol. 68, pp. 124–134, (1975).

Gupte, S. et al., "The Major Herpes Simplex Virus Type–1 DNA–binding Protein Is a Zinc Metalloprotein", *The Journal of Biological Chemistry*, vol. 266, No. 18, Jun. 25, 1991, pp. 11413–11416.

O'Donnell, M. et al., "Processive Replication of Single–stranded DNA Templates by the Herpes Simplex Virus-–induced DNA Polymerase", *The Journal of Biological Chemistry*, vol. 262, No. 9, Mar. 25, 1987, pp. 4252–4259.

O'Donnell, M. et al., "Interaction between the DNA Polymerase and Single–stranded DNA–binding Protein (Infected Cell Protein 8) of Herpes Simplex Virus 1", *The Journal of Biological Chemistry*, vol. 262, No. 9, Mar. 25, 1987, pp. 4260–4266.

Hernandez, T. et al., "Functional Interaction between the Herpes Simplex–1 DNA Polymerase and UL42 Protein", *The Journal of Biological Chemistry*, vol. 265, No. 19, Jul. 5, 1990, pp. 11227–11232.

Boehmer, P. et al., "Physical interaction between the herpes simplex virus 1 origin–binding protein and single–stranded DNA–binding protein ICP8", *Proc. Natl. Acad. Sci. USA*, vol. 90, pp. 8444–8448, Sep. 1993.

Rabkin, S. et al., "Nucleoprotein complex formed between herpes simplex virus UL9 protein and the origin of DNA replication: Inter– and intramolecular interactions", *Proc. Natl. Acad. Sci. USA*, vol. 88, pp. 10946–10950, Dec. 1991.

Makhov, A. et al., "The herpes simplex virus type 1 origin–binding protein carries out origin specific DNA unwinding and forms unwound stem–loop structures", *The EMBO Journal*, vol. 15, No. 7, pp. 1742–1750, (1996).

Dodson, M. et al., "The Herpes Simplex Virus Type I Origin Binding Protein", *The Journal of Biological Chemistry*, vol. 268, No. 2, Jan. 15, 1993, pp. 1213–1219.

Bruckner, R. et al., "The Herpes Simplex Virus 1 Origin Binding Protein: A DNA Helicase", *The Journal of Biological Chemistry*, vol. 266, No. 4, Feb. 5, 1991, pp. 2669–2674.

Boehmer, P. et al., "The Herpes Simplex Virus Type–1 Origin Binding Protein", *The Journal of Biological Chemistry*, vol. 268, No. 2, Jan. 15, 1993, pp. 1220–1225.

Fierer, D. et al., "Purification and Characterization of UL9, the Herpes Simplex Virus Type 1 Origin–Binding Protein", *Journal of Virology*, vol. 66, No. 7, Jul. 1992, pp. 3986–3995.

Makhov, A. et al., "Visualization of the Unwinding of Long DNA Chains by the Herpes Simplex Virus Type 1 UL9 Protein and ICP8", *J. Mol. Biol.*, vol. 258, pp. 789–799, (1996).

Abbotts, A. et al., "The origin–binding domain of the herpes simplex virus type 1 UL9 protein is not required for DNA helicase activity", *Journal of General Virology*, vol. 76, pp. 3125–3130, (1995).

| | |
|---|---|
| ∕∕∕∕∕∕∕ | Herpes replication origin sequence |
| ▬▬▬ | Complementary sequence to herpes replication origin sequence |
| - - - - | Single stranded tail on first strand |
| ——— | Single stranded tail on second strand |

FIGURE 2A

| SEQ. ID. NO. | | | | |
|---|---|---|---|---|
| 30 | OriS | 5'- AAAAGAAGTGAGAACGCGA|GCGGTTCGCACTTGTCC|AATATATATATATATTA|GGCGAAGTGCGAG|ACTGCCGCGTCCCGACTCCG -3' |
| 31 | OriL | 5'- ------A------|A|GCGGTTCGCACTTGTCC|-------A|GACAAAGTGCGAACGCT|TCGCGTTCTCACTTTTTT -3' |

Box III ... Box I ... Box II ... Box II ... Box I ... Box III

FIGURE 2B

Sequence comparison of UL9 protein binding sites with herpesvirus Ori sequence

SEQ. ID. NO.

| | | |
|---|---|---|
| 32 | HSU1S | AAAGAAGTGAGAACGCGA AGCGTTCGCACTTCGTCC CAATA --------TATATATAT----TATT-AGGGCGAAGTGCGAG--CACTG |
| 33 | L | AAAAAAGTGAGAACGGCGA AGCGTTCGCACTTGTCC TAATAA --------TATATATAT----TATT-AGGACAAGTGCGAA--CGCTT |
| 34 | HSU2S | AAAGAAGTGAGAACGCGA AGCGTTCGCACTTCGTCC TAATAG --------TATATATAT----TATT-AGGGCAAGTTGCGG--CACTG |
| 35 | L | AAAAAAGTGAGAACGCGA AGCGTTCGCACTTGTCC TAATAG --------TATATATAT----TATT-AGGGCAAGTGCGG--CACTG |
| 36 | UZU | TTGGCATGTGTCAAAC GACCGTTCGCACTTCTT C ------TATATATATATATATATATATATATATA----TATATA-GAGAAAGAGAGAG--AGTTT |
| 37 | HHU6 | TGACGTAAACGCCACGG CTTCGTTCTCCGTCCTCAA AAGTTTATAAAAAACTATATATATA-ATATACTAT GTACCTGAGGTGGACGACGATT |

FIGURE 2C

HSV$_S$ Box I  [SEQ. ID No. 13]
AGCGTTCGCACTTCGTCC
TCGCAAGCGTGAAGCAGG

HSV$_L$ Box I  [SEQ. ID No. 14]
AGCGTTCGCACTTTGTCC
TCGCAAGCGTGAAACAGG

HSV$_S$ Box II  [SEQ. ID No. 15]
GGGCGAAGTGCGAGCACTG
CCCGCTTCACGCTCGTGAC

HSV-1$_L$ Box II  [SEQ. ID No. 16]
GGACAAAGTGCGAACGCTT
CCTGTTTCACGCTTGCGAA

HSV-2$_L$ Box II  [SEQ. ID No. 17]
GGGCAAAGTTGCGGCACTG
CCCGTTTCAACGCCGTGAC

HSV$_S$ Box III  [SEQ. ID No. 18]
AAAGAAGTGAGAACGCG
TTTCTTCACTCTTGCGC

HSV-1$_L$ Box III  [SEQ. ID No. 19]
AAAAAAGTGAGAACGCG
TTTTTTCACTCTTGCGC

HSV-2$_L$ Box III  [SEQ. ID No. 20]
AAAAAAGTGAGAACGCC
TTTTTTCACTCTTGCGG

HSV$_S$ Boxes I and III  [SEQ. ID No. 21]
AAAGAAGTGAGAACGCGAAGCGTTCGCACTTCGTCC
TTTCTTCACTCTTGCGCTTCGCAAGCGTGAAGCAGG

FIGURE 2C (con't)

HSV-1$_L$ Boxes I and III          [SEQ. ID No. 22]
AAAAAAGTGAGAACGCGAAGCGTTCGCACTTTGTCC
TTTTTTCACTCTTGCGCTTCGCAAGCGTGAAACAGG HSV-2$_L$ Boxes I and III          [SEQ. ID No. 23]
AAAAAAGTGAGAACGCCAAGCGTTCGCACTTTGTCC
TTTTTTCACTCTTGCGGTTCGCAAGCGTGAAACAGG VZV Box I          [SEQ. ID No. 24]
ACCGTTCGCACTTTCTTT
TGGCAAGCGTGAAAGAAA VZV Box II          [SEQ. ID No. 25]
GAGAAAGAGAGAGAGTTT
CTCTTTCTCTCTCTCAAA VZV Box I'          [SEQ. ID No. 26]
TTTGGCATGTGTCCAACCACCGTTCGCACTTTCTTT
AAACCGTACACAGGTTGGTGGCAAGCGTGAAAGAAA HHV6 Box I          [SEQ. ID No. 27]
CTTCGTTCTCCCGTCCTCAA
GAAGCAAGAGGGCAGGAGTT HHV6 Box II          [SEQ. ID No. 28]
TGTACCTGAGGTGGACGACGATT
ACATGGACTCCACCTGCTGCTAA HHV6 Box I'          [SEQ. ID No. 29]
TGACGTAAACGCCACGCCTTCGTTCTCCCGTCCTCAA
ACTGCATTTGCGGTGCGGAAGCAAGAGGGCAGGAGTT

FIGURE 7

Substrate I:                                                        [SEQ. ID Nos. 2 and 1]

5'-CGCGAAGCGTTCGCACTTCGTCCCGCCTTCCTGCGCCTTCCTGT-3'
3'-GCGCTTCGCAAGCGTGAAGCAGGGCGACGCTCGTAC-5'

Substrate II:                                              [SEQ. ID Nos. 5 and 2]

5'-CGCGAAGCGTTCGCACTTCGTCCCGCCTTCCTGCGCCTTCCTGT-3'
3'-GCGCTTCGCAAGCGTGAAGCAGGGCG-5'

Substrate III:                                           [SEQ. ID Nos. 8 and 9]

5'-CATGCTCGCACGCGAAGCGTTCGCACTTCGTCCCGC-3'
3'-TGTCCTTCCGCGTCCTTCGCGCTTCGCAAGCGTGAAGCAGGGCG-5'

Substrate IV:                                          [SEQ. ID Nos. 6 and 7]

5'-CGCGAAGCGTTCGCACTTCGTCCCGC-3'
3'-GCGCTTCGCAAGCGTGAAGCAGGGCGCTTCCTGCACGCTCGTAC-5'

Substrate V:                                             [SEQ. ID Nos. 10 and 1]

5'-CGCGAAGCGTTCGCACTTCGTCCCGC-3'
3'-GCGCTTCGCAAGCGTGAAGCAGGGCGACGCTCGTAC-5'

Substrate VI:                                          [SEQ. ID Nos. 11 and 1]

5'-CGCGAAGCGTTCGCACTTCGTCCCGCCTTC-3'
3'-GCGCTTCGCAAGCGTGAAGCAGGGCGACGCTCGTAC-5'

Substrate VII:                                        [SEQ. ID Nos. 12 and 1]

5'-CGCGAAGCGTTCGCACTTCGTCCCGCCTTCCTGC-3'
3'-GCGCTTCGCAAGCGTGAAGCAGGGCGACGCTCGTAC-5'

\* Single-stranded DNA portions underlined
\* First strand shown on top and second strand shown on bottom FIGURE 12
I. Annealing Box I oligonucleotides
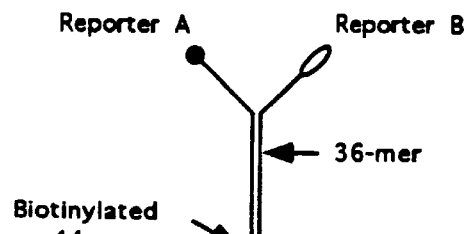
II. Immobilization of Box I substrate
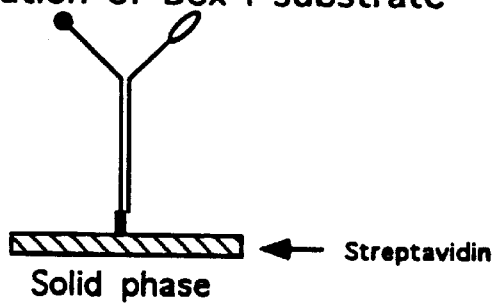
III. Box I Unwinding
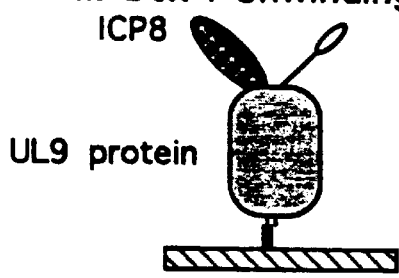
IV. Detection of UL9 helicase activity
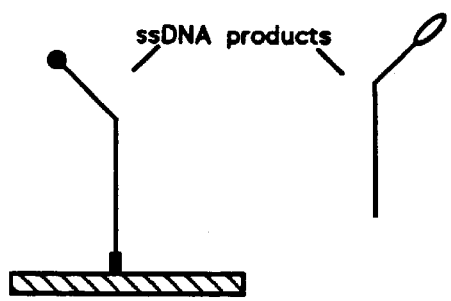

```
                             SEQUENCE LISTING (1) GENERAL INFORMATION:

(iii) NUMBER OF SEQUENCES:  37

(2) INFORMATION FOR SEQ ID NO: 1:

(i) SEQUENCE CHARACTERISTICS:
         (A) LENGTH: 36 nucleotides
         (B) TYPE: nucleic acid
         (C) STRANDEDNESS:  single
         (D) TOPOLOGY:  linear (xi) SEQUENCE DESCRIPTION: SEQ ID NO: 1:

CATGCTCGCA  GCGGGACGAA  GTGCGAACGC  TTCGCG                              36

(2) INFORMATION FOR SEQ ID NO: 2:

(i) SEQUENCE CHARACTERISTICS:
         (A) LENGTH: 44 nucleotides
         (B) TYPE: nucleic acid
         (C) STRANDEDNESS:  single
         (D) TOPOLOGY:  linear (xi) SEQUENCE DESCRIPTION: SEQ ID NO: 2:

CGCGAAGCGT  TCGCACTTCG  TCCCGCCTTC  CTGCGCCTTC  CTGT                    44

(2) INFORMATION FOR SEQ ID NO: 3:

(i) SEQUENCE CHARACTERISTICS:
         (A) LENGTH: 36 nucleotides
         (B) TYPE: nucleic acid
         (C) STRANDEDNESS:  single
         (D) TOPOLOGY:  linear (xi) SEQUENCE DESCRIPTION: SEQ ID NO: 3:

CATGCTCGCA  GCGGGACGAC  ACCTACGAGC  GCCCCG                              36

(2) INFORMATION FOR SEQ ID NO: 4:

(i) SEQUENCE CHARACTERISTICS:
         (A) LENGTH: 44 nucleotides
         (B) TYPE: nucleic acid
         (C) STRANDEDNESS:  single
         (D) TOPOLOGY:  linear (xi) SEQUENCE DESCRIPTION: SEQ ID NO: 4:

CGGGGCGCTC  GTAGGTGTCG  TCCCGCCTTC  CTGCGCCTTC  CTGT                    44

(2) INFORMATION FOR SEQ ID NO: 5:

(i) SEQUENCE CHARACTERISTICS:
         (A) LENGTH: 26 nucleotides
         (B) TYPE: nucleic acid
         (C) STRANDEDNESS:  single
         (D) TOPOLOGY:  linear (xi) SEQUENCE DESCRIPTION: SEQ ID NO: 5:

GCGGGACGAA  GTGCGAACGC  TTCGCG                                          26
```

(2) INFORMATION FOR SEQ ID NO: 6:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO: 6:

```
CGCGAAGCGT TCGCACTTCG TCCCGC                                    26
```

(2) INFORMATION FOR SEQ ID NO: 7:

(i) SEQUENCE CHARACTERISTICS:
        (A) LENGTH: 44 nucleotides
        (B) TYPE: nucleic acid
        (C) STRANDEDNESS: single
        (D) TOPOLOGY: linear (xi) SEQUENCE DESCRIPTION: SEQ ID NO: 7:

```
CATGCTCGCA CGTCCTTCGC GGGACGAAGT GCGAACGCTT CGCG                44
```

(2) INFORMATION FOR SEQ ID NO: 8:

(i) SEQUENCE CHARACTERISTICS:
        (A) LENGTH: 36 nucleotides
        (B) TYPE: nucleic acid
        (C) STRANDEDNESS: single
        (D) TOPOLOGY: linear (xi) SEQUENCE DESCRIPTION: SEQ ID NO: 8:

```
CATGCTCGCA CGCGAAGCGT TCGCACTTCG TCCCGC                         36
```

(2) INFORMATION FOR SEQ ID NO: 9:

(i) SEQUENCE CHARACTERISTICS:
        (A) LENGTH: 44 nucleotides
        (B) TYPE: nucleic acid
        (C) STRANDEDNESS: single
        (D) TOPOLOGY: linear (xi) SEQUENCE DESCRIPTION: SEQ ID NO: 9:

```
GCGGGACGAA GTGCGAACGC TTCGCGCTTC CTGCGCCTTC CTGT                44
```

(2) INFORMATION FOR SEQ ID NO: 10:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO: 10:

```
CGCGAAGCGT TCGCACTTCG TCCCGC                                    26
```

(2) INFORMATION FOR SEQ ID NO: 11:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO: 11:

```
CGCGAAGCGT TCGCACTTCG TCCCGCCTTC                                30
```

(2) INFORMATION FOR SEQ ID NO: 12:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (xi) SEQUENCE DESCRIPTION: SEQ ID NO: 12:

CGCGAAGCGT TCGCACTTCG TCCCGCCTTC CTGC                        34

(2) INFORMATION FOR SEQ ID NO: 13:

(i) SEQUENCE CHARACTERISTICS:
        (A) LENGTH: 18 nucleotides
        (B) TYPE: nucleic acid
        (C) STRANDEDNESS: double
        (D) TOPOLOGY: linear (xi) SEQUENCE DESCRIPTION: SEQ ID NO: 13:

AGCGTTCGCA CTTCGTCC                                          18

(2) INFORMATION FOR SEQ ID NO: 14:

(i) SEQUENCE CHARACTERISTICS:
        (A) LENGTH: 18 nucleotides
        (B) TYPE: nucleic acid
        (C) STRANDEDNESS: double
        (D) TOPOLOGY: linear (xi) SEQUENCE DESCRIPTION: SEQ ID NO: 14:

AGCGTTCGCA CTTTGTCC                                          18

(2) INFORMATION FOR SEQ ID NO: 15:

(i) SEQUENCE CHARACTERISTICS:
        (A) LENGTH: 19 nucleotides
        (B) TYPE: nucleic acid
        (C) STRANDEDNESS: double
        (D) TOPOLOGY: linear (xi) SEQUENCE DESCRIPTION: SEQ ID NO: 15:

GGGCGAAGTGC GAGCACTG                                      19

(2) INFORMATION FOR SEQ ID NO: 16:

(i) SEQUENCE CHARACTERISTICS:
        (A) LENGTH: 19 nucleotides
        (B) TYPE: nucleic acid
        (C) STRANDEDNESS: double
        (D) TOPOLOGY: linear (xi) SEQUENCE DESCRIPTION: SEQ ID NO: 16:

GGACAAAGTG CGAACGCTT                                      19

(2) INFORMATION FOR SEQ ID NO: 17:

(i) SEQUENCE CHARACTERISTICS:
        (A) LENGTH: 19 nucleotides
        (B) TYPE: nucleic acid
        (C) STRANDEDNESS: double
        (D) TOPOLOGY: linear (xi) SEQUENCE DESCRIPTION: SEQ ID NO: 17:

GGGCAAAGTT GCGGCACTG                                      19

(2) INFORMATION FOR SEQ ID NO: 18:

(i) SEQUENCE CHARACTERISTICS:
        (A) LENGTH: 17 nucleotides
        (B) TYPE: nucleic acid
        (C) STRANDEDNESS: double
        (D) TOPOLOGY: linear (xi) SEQUENCE DESCRIPTION: SEQ ID NO: 18:

AAAGAAGTGA GAACGCG       17

(2) INFORMATION FOR SEQ ID NO: 19:

(i) SEQUENCE CHARACTERISTICS:
        (A) LENGTH: 17 nucleotides
        (B) TYPE: nucleic acid
        (C) STRANDEDNESS: double
        (D) TOPOLOGY: linear (xi) SEQUENCE DESCRIPTION: SEQ ID NO: 19:

AAAAAAGTGA GAACGCG       17

(2) INFORMATION FOR SEQ ID NO: 20:

(i) SEQUENCE CHARACTERISTICS:
        (A) LENGTH: 17 nucleotides
        (B) TYPE: nucleic acid
        (C) STRANDEDNESS: double
        (D) TOPOLOGY: linear (xi) SEQUENCE DESCRIPTION: SEQ ID NO: 20:

AAAAAAGTGA GAACGCC       17

(2) INFORMATION FOR SEQ ID NO: 21:

(i) SEQUENCE CHARACTERISTICS:
        (A) LENGTH: 36 nucleotides
        (B) TYPE: nucleic acid
        (C) STRANDEDNESS: double
        (D) TOPOLOGY: linear (xi) SEQUENCE DESCRIPTION: SEQ ID NO: 21:

AAAGAAGTGA GAACGCGAAG CGTTCGCACT TCGTCC       36

(2) INFORMATION FOR SEQ ID NO: 22:

(i) SEQUENCE CHARACTERISTICS:
        (A) LENGTH: 36 nucleotides
        (B) TYPE: nucleic acid
        (C) STRANDEDNESS: double
        (D) TOPOLOGY: linear (xi) SEQUENCE DESCRIPTION: SEQ ID NO: 22:

AAAAAAGTGA GAACGCGAAG CGTTCGCACT TTGTCC       36

(2) INFORMATION FOR SEQ ID NO: 23:

(i) SEQUENCE CHARACTERISTICS:
        (A) LENGTH: 36 nucleotides
        (B) TYPE: nucleic acid
        (C) STRANDEDNESS: double
        (D) TOPOLOGY: linear (xi) SEQUENCE DESCRIPTION: SEQ ID NO: 23:

AAAAAAGTGA GAACGCCAAG CGTTCGCACT TTGTCC       36

(2) INFORMATION FOR SEQ ID NO: 24:

(i) SEQUENCE CHARACTERISTICS:
        (A) LENGTH: 18 nucleotides
        (B) TYPE: nucleic acid
        (C) STRANDEDNESS: double
        (D) TOPOLOGY: linear (xi) SEQUENCE DESCRIPTION: SEQ ID NO: 24:

ACCGTTCGCA CTTTCTTT                                                               18

(2) INFORMATION FOR SEQ ID NO: 25:

(i) SEQUENCE CHARACTERISTICS:
        (A) LENGTH: 18 nucleotides
        (B) TYPE: nucleic acid
        (C) STRANDEDNESS: double
        (D) TOPOLOGY: linear (xi) SEQUENCE DESCRIPTION: SEQ ID NO: 25:

GAGAAAGAGA GAGAGTTT                                                               18

(2) INFORMATION FOR SEQ ID NO: 26:

(i) SEQUENCE CHARACTERISTICS:
        (A) LENGTH: 36 nucleotides
        (B) TYPE: nucleic acid
        (C) STRANDEDNESS: double
        (D) TOPOLOGY: linear (xi) SEQUENCE DESCRIPTION: SEQ ID NO: 26:

TTTGGCATGT GTCCAACCAC CGTTCGCACT TTCTTT                                           36

(2) INFORMATION FOR SEQ ID NO: 27:

(i) SEQUENCE CHARACTERISTICS:
        (A) LENGTH: 20 nucleotides
        (B) TYPE: nucleic acid
        (C) STRANDEDNESS: double
        (D) TOPOLOGY: linear (xi) SEQUENCE DESCRIPTION: SEQ ID NO: 27:

CTTCGTTCTC CCGTCCTCAA                                                             20

(2) INFORMATION FOR SEQ ID NO: 28:

(i) SEQUENCE CHARACTERISTICS:
        (A) LENGTH: 23 nucleotides
        (B) TYPE: nucleic acid
        (C) STRANDEDNESS: double
        (D) TOPOLOGY: linear (xi) SEQUENCE DESCRIPTION: SEQ ID NO: 28:

TGTACCTGAG GTGGACGACG ATT                                                         23

(2) INFORMATION FOR SEQ ID NO: 29:

(i) SEQUENCE CHARACTERISTICS:
        (A) LENGTH: 37 nucleotides
        (B) TYPE: nucleic acid
        (C) STRANDEDNESS: double
        (D) TOPOLOGY: linear (xi) SEQUENCE DESCRIPTION: SEQ ID NO: 29:

TGACGTAAAC GCCACGCCTT CGTTCTCCCG TCCTCAA                                          37

(2) INFORMATION FOR SEQ ID NO: 30:

-continued (i) SEQUENCE CHARACTERISTICS:
        (A) LENGTH: 93 nucleotides
        (B) TYPE: nucleic acid
        (C) STRANDEDNESS: single
        (D) TOPOLOGY: linear (xi) SEQUENCE DESCRIPTION: SEQ ID NO: 30:

AAAAGAAGTG AGAACGCGAA GCGTTCGCAC TTCGTCCCAA TATATATATA          50

TTATTAGGGC GAAGTGCGAG CACTGGCGCC GTGCCCGACT CCG                 93

(2) INFORMATION FOR SEQ ID NO: 31:

(i) SEQUENCE CHARACTERISTICS:
        (A) LENGTH: 59 nucleotides
        (B) TYPE: nucleic acid
        (C) STRANDEDNESS: single
        (D) TOPOLOGY: linear (xi) SEQUENCE DESCRIPTION: SEQ ID NO: 31:

AAAGCGTTCG CACTTTGTCC TAGGACAAAG TGCGAACGCT TCGCGTTCTC          50

ACTTTTTTT                                                       59

(2) INFORMATION FOR SEQ ID NO: 32:

(i) SEQUENCE CHARACTERISTICS:
        (A) LENGTH: 74 nucleotides
        (B) TYPE: nucleic acid
        (C) STRANDEDNESS: single
        (D) TOPOLOGY: linear (xi) SEQUENCE DESCRIPTION: SEQ ID NO: 32:

AAAGAAGTGA GAACGCGAAG CGTTCGCACT TCGTCCCAAT ATATATATAT          50

TATTAGGGCG AAGTGCGAGC ACTG                                      74

(2) INFORMATION FOR SEQ ID NO: 33:

(i) SEQUENCE CHARACTERISTICS:
        (A) LENGTH: 75 nucleotides
        (B) TYPE: nucleic acid
        (C) STRANDEDNESS: single
        (D) TOPOLOGY: linear (xi) SEQUENCE DESCRIPTION: SEQ ID NO: 33:

AAAAAAGTGA GAACGCGAAG CGTTCGCACT TTGTCCTAAT AATATATATA          50

TTATTAGGAC AAAGTGCGAA CGCTT                                     75

(2) INFORMATION FOR SEQ ID NO: 34:

(i) SEQUENCE CHARACTERISTICS:
        (A) LENGTH: 75 nucleotides
        (B) TYPE: nucleic acid
        (C) STRANDEDNESS: single
        (D) TOPOLOGY: linear (xi) SEQUENCE DESCRIPTION: SEQ ID NO: 34:

AAAGAAGTGA GAACGCGAAG CGTTCGCACT TCGTCCTAAT AGTATATATA          50

TTATTAGGGC AAAGTTGCGG CACTG                                     75

(2) INFORMATION FOR SEQ ID NO: 35:

(i) SEQUENCE CHARACTERISTICS:
        (A) LENGTH: 75 nucleotides
        (B) TYPE: nucleic acid
        (C) STRANDEDNESS: single

```
            (D) TOPOLOGY:  linear (xi) SEQUENCE DESCRIPTION: SEQ ID NO: 35:

AAAAAAGTGA   GAACGCCAAG   CGTTCGCACT   TTGTCCTAAT   AGTATATATA           50

TTATTAGGGC   AAAGTTGCGG   CACTG                                          75

(2) INFORMATION FOR SEQ ID NO: 36:

(i) SEQUENCE CHARACTERISTICS:
            (A) LENGTH: 87 nucleotides
            (B) TYPE: nucleic acid
            (C) STRANDEDNESS:  single
            (D) TOPOLOGY:  linear (xi) SEQUENCE DESCRIPTION: SEQ ID NO: 36:

TTTGGCATGT   GTCCAACCAC   CGTTCGCACT   TTCTTTCTAT   ATATATATAT           50

ATATATATAT   ATATATATAG   AGAAAGAGAG   AGAGTTT                           87

(2) INFORMATION FOR SEQ ID NO: 37:

(i) SEQUENCE CHARACTERISTICS:
            (A) LENGTH: 96 nucleotides
            (B) TYPE: nucleic acid
            (C) STRANDEDNESS:  single
            (D) TOPOLOGY:  linear (xi) SEQUENCE DESCRIPTION: SEQ ID NO: 37:

TGACGTAAAC   GCCACGCCTT   CGTTCTCCCG   TCCTCAATAA   GTTTATTAAA           50

AAACTATATA   TATAATATAC   TATTGTACCT   GAGGTGGACG   ACGATT               96
```

SUBSTRATE FOR DETECTING UL9 HELICASE ACTIVITY

BACKGROUND OF THE INVENTION

1. Field of Invention

The present invention relates to a substrate for detecting helicase activity in a herpes simplex virus helicase as well as methods for using the substrates.

2. Description of Related Art

Helicases are a class of enzymes that catalyze unwinding of duplex DNA by disrupting the hydrogen bonds that hold the two strands of duplex DNA together. Matson and Kaiser-Rogers, Annu. Rev. Biochem. 59: 289–329 (1994); Lohman and Bjornson, Annu. Rev. Biochem. 65: 169–214 (1996). This unwinding process is important to generate single stranded DNA regions, which are subsequently utilized by other enzymes during DNA replication, repair, and recombination. Kornberg and Baker, DNA Replication, $2^{nd}$ ed., W. H. Freeman and Co., New York (1992). Although the detailed unwinding mechanisms of helicases are not fully understood, it is clear that in order to unwind duplex DNA continuously, a helicase enzyme translocates, along the DNA by hydrolyzing nucleotide 5'-triphosphate (NTP or dNTP). The helicases thus far identified also exhibit a specific directionality, i.e., 3'-5' or 5'-3', for unwinding duplex DNA.

Helicase activity can be measured as either displacement of single stranded DNA (ssDNA) from duplex DNA or as continuous unwinding of duplex DNA. The most common assay is a gel-based helicase assay using a partially duplex M13 or ΦX174 DNA substrate. The ssDNA or ssRNA product, which is radiolabeled, can be detected by its altered mobility during electrophoresis on a nondenaturing gel, or by sensitivity to ssDNA-specific nucleases. Abdel-Monem et al., Eur. J. Biochem. 65, 441–449 (1976); Doguet et al., Cold Spring Harbor Symp. Quant. Biol. 43, 335–343 (1979); Kuhn et al., Cold Spring Harbor Symp. Quant. Biol. 43, 63–67 (1979); Palas et al., J. Biol. Chem. 265, 3447–3454 (1990); Venkatesan et al., J. Biol. Chem. 257, 12426–12434 (1982); Matson et al., J. Biol. Chem. 258, 14017–14024 (1983). Direct measurement by electron microscopy has also been employed to visualize the regions of DNA unwound by helicases. Taylor and Smith, Cell, 22, 447–457 (1980); Baumel et al., Eur. J. Biochem. 138, 247–251 (1984); Benz et al., Acta Microbiologica Polonica 35, 191–197 (1986); Dodson et al., Science, 238, 964–967 (1987); Runyon et al., Proc. Natl. Acad. Sci. USA, 87, 6383–6387(1990).

Several continuous fluorometric assays have also been developed for measuring helicase activity. One assay requires a single-strand DNA binding (SSB) protein as the reporter molecule. Roman and Kowalczykowski, Biochemistry, 28, 2863–2873 (1989). As the duplex DNA is unwound, the SSB protein binds to the ssDNA products, and its intrinsic fluorescent emission is quenched. Another assay utilizes duplex DNA whose complementary ends are tagged with different fluorescent moieties. Houston and Kodadek, Proc. Natl. Acad. Sci. USA, 91, 5471–5474 (1994); Bjornson et al., Biochemistry, 33, 14306–14316 (1994). A change in the overall fluorescent emission is detected and quantitated as the duplex DNA is unwound. Similarly, DNA substrates can be modified with 2-aminopurine substituted in place of adenine. Raney et al., Proc. Natl. Acad. Sci. USA, 91, 6644–6648 (1994). The 2-aminopurine exhibits fluorescence quenching when the analog forms hydrogen bonds with thymine residues. Single stranded DNA products generated by a helicase will remove this quenching effect, resulting in an increase in fluorescent emission. Recently, different fluorophores that bind to duplex DNA have also been evaluated as reporter molecules during unwinding Eggleston et al., Nucleic acids Res. 24, 1179–1186 (1996). In this assay, the fluorescent reporter dye initially bound to the substrate is converted to free molecules in solution as the helicase unwinds the substrate, resulting in a reduction of the fluorescence signal.

Although the assays described above have been widely employed for purifying or characterizing several different types of helicases, these assays lack the ability to selectively test for a particular protein exhibiting helicase activity. A need thus exists for an assay which is specific for a particular type or class of helicase.

Herpes viruses are significant infectious agents which cause a variety of diseases in humans and other mammals. Herpes simplex viruses (HSVs) were the first of the human herpes viruses to be discovered and have been thoroughly characterized. The replication of HSV-1 DNA serves as an excellent model system to understand DNA replication by other herpes viruses. The herpes simplex virus type 1 (HSV-1) genome consists of 152 kb of linear dsDNA and contains three highly homologous origins of replication; $ori_L$ and two copies of $ori_S$. Stow, EMBO J. 1, 863–867 (1982); Stow, Virology, 130, 427–438 (1983); Stow, J. Gen. Virol. 66, 3142; Weller et al., Mol. Cell. Biol. 5, 930–942 (1988); Challberg and Kelly, Annu. Rev. Biochem. 58, 671–717. The virus also encodes a 94-kDa origin binding protein, the product of the UL9 gene, which has been shown to be essential for replication of HSV-1 DNA in vivo. Elias et al., Proc. Natl. Acad. Sci. USA 83, 6322–6326 (1986); Olivo et al., Proc. Natl. Acad. Sci. USA 85, 5414–5418 (1988); Wu et al., J. Virol. 62, 435–443 (1988); Stow, J. Gen. Virol. 73, 313–321 (1992). The UL9 protein has also been shown to specifically and cooperatively bind the two inverted pentanucleotide repeats in Boxes I and II of $ori_S$ which are separated from each other by an A/T-rich sequence of 18 nucleotides (nt), illustrated in FIG. 2A. Elias et al., J. Biol. Chem. 265, 17167–17173; Bruckner et al., J. Biol. Chem. 266, 2669–2674 (1991); Fierer and Challberg, J. Virol. 66, 39868–3995; Hazuda et al., J. Biol. Chem. 265, 14309–14315 (1992). Another herpes viral origin, $ori_L$ contains a second copy of Box I in place of Box II, also illustrated in FIG. 2A.

In addition to its origin binding activity, the UL9 protein has been shown to exhibit DNA-dependent ATPase activity and 3'-5' helicase activity using a partially duplex M13 DNA substrate. Bruckner et al., J. Biol. Chem. 266, 2669–2674 (1991); Fierer and Challberg, J. Virol. 66, 39868–3995; Dodson and Lehman, J. Biol. Chem. 268, 1213–1219 (1993); Boehmer et al., J. Biol. Chem. 268, 1220–1225 (1993).

Despite the UL9 protein's intrinsic 3'-5' helicase activity on the partially duplex M13 DNA substrate, attempts to get the UL9 protein to unwind the viral origin sequence or the duplex Box I element have been unsuccessful. Attempts to demonstrate the specific unwinding of $ori_S$ by the UL9 protein were patterned after similar studies with the simian virus 40 large T antigen. In this system, a double hexamer protein binds, and by virtue of its helicase activity, unwinds the SV40 origin of replication. Stillman, Annu. Rev. Cell Biol. 5, 915–918 (1989); Borowiec et al., Cell 60, 181–184 (1990). In vitro, a single stranded binding protein (SSB), such as either the homologous RP-A or the heterologous E. coli SSB, is required to maintain the separated strands. However, similar experiments with the herpes UL9 protein using both linear duplexes containing the $ori_S$ sequence or plasmids into which the $ori_S$ sequence had been inserted failed to demonstrate specific unwinding by the UL9 protein either alone or in the presence of the herpes SSB, ICP8, or heterologous SSBs. A need thus also exists for a method for detecting helicase activity in the UL9 protein when bound to a herpes origin of replication.

The HSV-1 single strand DNA binding protein, ICP8, was one of the first HSV-1 DNA replication proteins to be identified and has been shown to be required for the replication of HSV-1 DNA in vivo. Bayliss et al., Virology, 68, 124–134 (1975); Quinn and McGeoch, Nucleic Acids Res. 13, 8143–8163. Biochemical studies have shown that ICP8 binds single-stranded DNA rapidly and cooperatively and with at least fivefold greater affinity than double-stranded DNA. Ruyechan, J. Virol. 46, 661–666 (1983); Lee and Knipe, J. Virol. 54, 731–738 (1985). The DNA binding site size for ICP8 has been estimated from nuclease protection and electron microscopy to be 12–22 nucleotides. Boehmer and Lehman, J. Virol. 67, 711–715 (1993); Dutch and Lehman, J. Virol. 67, 6945–6949 (1993); Hernandez and Lehman, J. Biol. Chem. 265,11227–11232 (1990); O'Donnell et al., J. Biol. Chem. 262, 4260–4266 (1987). ICP8 is believed to play a key role in the assembly of the HSV-1 DNA replication proteins into prereplicative sites that are precursors to discrete nuclear locations in which viral DNA replication occurs. Quinlan et al., Cell, 36, 857–868 (1984); Gao and Knipe, J. Virol. 63, 5258–5267 (1989); Olivo et al., J. Virol. 63,196–204 (1989); de Bruyn Kops and Knipe, Cell, 55, 857–868 (1988). Further elucidation of the role ICP8 plays in the replication of HSV-1 is needed.

SUMMARY OF THE INVENTION

A UL9 substrate for detecting helicase activity in a UL9 protein is provided. In one embodiment, the substrate includes a first strand including a herpes replication origin sequence and a first single stranded tail; and a second strand including a sequence complementary to the herpes replication origin sequence.

In one variation, the first single stranded tail is 3' relative to the herpes replication origin sequence. The second strand may optionally further include a single stranded tail. The single stranded tail on the second strand may be 3' or 5' relative to the sequence complementary to the herpes replication origin sequence.

In another variation, the first single stranded tail is 5' relative to the herpes replication origin sequence. The second strand may optionally further include a single stranded tail. The single stranded tail on the second strand may be 3' or 5' relative to the sequence complementary to the herpes replication origin sequence.

The UL9 substrate may optionally further include at least one detectable marker attached to at least one of the first and second strands. The UL9 substrate may also optionally be attached to a solid support.

A method for detecting UL9 helicase activity is provided. In one embodiment, the method includes contacting a sample believed to contain the UL9 protein with a substrate according to the present invention, ATP and ICP8; and detecting unwinding of the substrate, wherein unwinding of the substrate indicates the presence of UL9 helicase activity.

A method for detecting an ability of a chemical entity to inhibit UL9 helicase activity is also provided. In one embodiment, the method includes contacting a sample containing the UL9 protein, a substrate according to the present invention, ATP and ICP8 with a chemical entity; and detecting unwinding of the substrate. By comparing the level or rate of unwinding of the substrate in the presence of the chemical entity to the level or rate of unwinding of the substrate in the absence of the chemical entity, the ability of a chemical entity to inhiibit UL9 helicase activity can be evaluated.

A method for detecting herpes infected samples is also provided. In one embodiment, the method includes taking an immobilized UL9 substrate; contacting a cell lysate with the UL9 substrate; and detecting UL9 and ICP8 bound to the UL9 substrate, the presence of UL9 and ICP8 indicating the presence of herpes virus in the cell lysate.

According to the different methods of the present invention, any UL9 substrate according to the present invention can be employed.

The present invention also relates to one or more kits for performing the above described methods. These kits can include one or more of the components used to perform the methods, such as the substrate optionally attached to a solid support, UL9, ICP8 and/or ATP.

BRIEF DESCRIPTION OF THE FIGURES

FIG. 1A illustrates a UL9 substrate with a 3' single stranded tail on a first sequence containing a herpes replication origin sequence.

FIG. 1B illustrates a UL9 substrate with a 3' single stranded tail on the first sequence containing a herpes replication origin sequence and a 5' single stranded tail on the second sequence which is at least partially complementary to the first sequence at the herpes replication origin sequence.

FIG. 1C illustrates a UL9 substrate with a 3' single stranded tail on the first sequence containing a herpes replication origin sequence and a 3' single stranded tail on the second sequence which is at least partially complementary to the first sequence at the herpes replication origin sequence.

FIG. 1D illustrates a UL9 substrate with a 5' single stranded tail on the first sequence containing a herpes replication origin sequence.

FIG. 1E illustrates a UL9 substrate with a 5' single stranded tail on the first sequence containing a herpes replication origin sequence and a 3' single stranded tail on the second sequence which is at least partially complementary to the first sequence at the herpes replication origin sequence.

FIG. 1F illustrates a UL9 substrate with a 5' single stranded tail on the first sequence containing a herpes replication origin sequence and a 5' single stranded tail on the second sequence which is at least partially complementary to the first sequence at the herpes replication origin sequence.

FIG. 1G illustrates a UL9 substrate with 5' and 3' single stranded tails on the first sequence containing a herpes replication origin sequence and 5' and 3' single stranded tails on the second sequence which is at least partially complementary to the first sequence at the herpes replication origin sequence.

FIG. 2A illustrates the nucleotide sequence of HSV-1 replication origins $ori_S$ and $ori_L$.

FIG. 2B illustrates a sequence comparison of UL9 binding sites with alphaherpesvirus origin sequences. HSV1S, HSV-1 $ori_S$; HSV1L, HSV-1 $ori_L$; HSV2S, HSV-2 $ori_S$; HSV2L, HSV-2 $ori_L$; VZV, varicella-zoster virus $ori_S$; HHV6, human herpesvirus 6 ori.

FIG. 2C provides a list of herpes replication origin sequences and their complements which may be used in the substrates of the present invention.

FIG. 7 illustrates different UL9 substrates.

FIG. 12 illustrates an embodiment of a high throughput assay system using an immobilized UL9 substrate.

DETAILED DESCRIPTION

Despite the herpes UL9 protein exhibiting intrinsic 3'-5' helicase activity on a partially duplex M13 DNA substrate, previous attempts to get the UL9 protein to unwind a duplex containing a HSV-1 replication origin sequence, such as viral origin sequences ($ori_S$ or $ori_L$) has been unsuccessful.

The present invention relates to UL9 substrates which can be used in combination with ICP8 and ATP to detect helicase activity in the UL9 protein. More specifically, the present invention relates to substrates which comprise at least a first strand which includes a herpes replication origin sequence and a first single stranded tail; and a second strand which includes a sequence complementary to the herpes replication origin sequence.

Figure 1A:
FIGS. 1A–G illustrate different UL9 substrates according to the present invention.

In one embodiment, the substrate comprises a first strand which includes a herpes replication origin sequence and a first single stranded tail 3' relative to the herpes replication origin sequence; and a second strand which includes a sequence complementary to the herpes replication origin sequence. FIG. 1A illustrates a UL9 substrate with a 3' single stranded tail on the first strand containing the herpes replication origin sequence.

Figure 1B:
Figure 1C:

According to this embodiment, the second strand of the substrate may optionally include a second single stranded tail 5' or 3' relative to the herpes replication origin sequence. FIGS. 1B and 1C illustrate UL9 substrates according to this embodiment with a 3' single stranded tail on the first strand containing a herpes replication origin sequence and a 5' or 3' single stranded tail on the second strand which is at least partially complementary to the first sequence at the herpes replication origin sequence.

According to this embodiment, the first single stranded tail preferably has a length of at least about 8 nucleotides and more preferably at least about 12 nucleotides. It is currently preferred that the first single stranded tail have a length of about 18 nucleotides. It is noted, however, that the first single stranded tail can be longer than 18 nucleotides. For example, the tail may be used to attach the substrate to a solid support or to a attach a detectable marker to the substrate. The first single stranded tail preferably has a length between about 8 and 100 nucleotides, more preferably between about 8 and 50 nucleotides, and most preferably between about 8 and 36 nucleotides. The particular preferred length of the first single stranded tail depends on the particular method in which the substrate is used and can be determined by an iterative analysis based on the teaching of the present invention.

In one variation, the first strand including the single stranded tail forms all or part of a plasmid to which the second strand hybridizes. In this variation, the plasmid forming the first strand may be 2000–7000 nucleotides in length, or longer.

The second single stranded tail preferably has a length of at least about 4 nucleotides, more preferably at least about 8 nucleotides, and most preferably at least about 10 nucleotides. It is currently preferred that the second single stranded tail have a length different than the first single stranded tail so that it is possible to separate the first and second strands based on size. The second single stranded tail may optionally be used to attach the substrate to a solid support or to a attach a detectable marker to the substrate. The second single stranded tail preferably has a length between about 4 and 100 nucleotides, more preferably between about 4 and 50 nucleotides, and most preferably between about 4 and 36 nucleotides. The particular preferred length of the second single stranded tail depends on the particular method in which the substrate is used and can be determined by an iterative analysis based on the teaching of the present invention.

In one variation, the second strand including the single stranded tail forms all or part of a plasmid to which the first strand hybridizes. In this variation, the plasmid forming the second strand may be 2000–7000 nucleotides in length, or longer.

Figure 1D:

In another embodiment, the substrate comprises a first strand which includes a herpes replication origin sequence and a first single stranded tail 5' relative to the herpes replication origin sequence; and a second strand which includes a sequence complementary to the herpes replication origin sequence. FIG. 1D illustrates a UL9 substrate with a 5' single stranded tail on the first strand containing a herpes replication origin sequence.

Figure 1E:
Figure 1F:

According to this embodiment, the second strand of the substrate may optionally include a second single stranded tail 3' or 5' relative to the herpes replication origin sequence. FIGS. 1E and 1F illustrate UL9 substrates according to this embodiment with a 3' single stranded tail on the first strand containing a herpes replication origin sequence and a 3' or 5' single stranded tail on the second strand which is at least partially complementary to the first strand at the herpes replication origin sequence.

According to this embodiment, the first single stranded tail preferably has a length of at least about 8 nucleotides and more preferably at least about 12 nucleotides. It is currently preferred that the first single stranded tail have a length of about 18 nucleotides. It is noted, however, that the first single stranded tail can be longer than 18 nucleotides. For example, the tail may be used to attach the substrate to a solid support or to a attach a detectable marker to the substrate. The first single stranded tail preferably has a length between about 8 and 100 nucleotides, more preferably between about 8 and 50 nucleotides, and most preferably between about 8 and 36 nucleotides. The particular preferred length of the first single stranded tail depends on the particular method in which the substrate is used and can be determined by an iterative analysis based on the teaching of the present invention.

In one variation, the first strand including the single stranded tail forms all or part of a plasmid to which the second strand hybridizes. In this variation, the plasmid forming the first strand may be 2000–7000 nucleotides in length, or longer.

The second single stranded tail preferably has a length of at least about 4 nucleotides, more preferably at least about 8 nucleotides, and most preferably at least about 10 nucleotides. It is currently preferred that the second single stranded tail have a length different than the first single stranded tail so that it is possible to separate the first and second strands based on size. The second single stranded tail may optionally be used to attach the substrate to a solid support or to a attach a detectable marker to the substrate. The second single stranded tail preferably has a length between about 4 and 100 nucleotides, more preferably between about 4 and 50 nucleotides, and most preferably between about 4 and 36 nucleotides. The particular preferred length of the second single stranded tail depends on the particular method in which the substrate is used and can be determined by an iterative analysis based on the teaching of the present invention.

In one variation, the second strand including the single stranded tail forms all or part of a plasmid to which the first strand hybridizes. In this variation, the plasmid forming the second strand may be 2000–7000 nucleotides in length, or longer.

Figure 1G:

With regard to the UL9 substrate embodiments described above and illustrated in FIGS. 1A–G, it is noted that these substrates can further include additional single stranded tails other than the ones specified. For example, as illustrated in FIG. 1G, the UL9 substrate may have 5' and 3' single stranded tails on the first sequence containing the herpes replication origin sequence and 5' and 3' single stranded tails on the second sequence. These additional tails may be used to attach the substrate to a solid support or to a attach a detectable marker to the substrate.

As will be discussed herein, the UL9 substrates of the present invention may also include one or more detectable markers, linking moieties for attaching the substrate to a solid support as well as any other additional moiety which may be desirable for a particular application of the substrate.

The UL9 protein is known to specifically and cooperatively bind to two inverted pentanucleotide repeats in Boxes I and II of $ori_S$ which are separated from each other by an A/T-rich sequence of 18 nucleotides (nt). Elias et al., J. Biol. Chem. 265, 17167–17173; Bruckner et al., J. Biol. Chem. 266, 2669–2674 (1991); Fierer and Challberg, J. Virol. 66, 39868–3995; Hazuda et al., J. Biol. Chem. 265, 14309–14315 (1992). Another herpes viral origin, $ori_L$ contains a second copy of Box I in place of Box II. FIG. 2A illustrates the nucleotide sequence of HSV-1 replication origins, $ori_S$(SEQ. ID. NO. 30) and $ori_L$(SEQ. ID. NO. 31). Boxes I and II are strong UL9 protein binding sites. Box III is a weaker binding site for the UL9 protein. The X's indicated in the $ori_S$ sequence refer to nucleotides that are absent from $ori_S$ but present in $ori_L$. The sequences shown in Boxes I, II and III of $ori_S$(SEQ. ID. NO. 30) and $ori_L$(SEQ. ID. NO. 31) of FIG. 2A can be employed as the herpes replication origin sequences in substrates according to the present invention.

FIG. 2B illustrates a sequence comparison of UL9 binding sites with alphaherpesvirus origin sequences. HSV1S, HSV-1 $ori_S$(SEQ ID NO. 32); HSV1L, HSV-1 $ori_L$(SEQ. ID. NO. 33); HSV2S, HSV-2 $ori_S$(SEQ. ID. NO. 34); HSV2L, HSV-2 $ori_L$(SEQ. ID. NO. 35); VZV, varicella-zoster virus $ori_S$(SEQ. ID. NO. 36); HHV6, human herpesvirus 6 ori (SEQ. ID. NO. 37). The strong UL9 binding sites for each of these viruses is circled in a box. The sequences shown in the boxes of FIG. 2B for HSV2S, HSV2L, VZV and HHV6 can also be employed as herpes replication origin sequences in substrates of the present invention.

FIG. 2C provides a list of herpes replication origin box sequences (top strand) and their complements (bottom strand) which may be used in the substrates of the present invention. Subsequences of the replication origin box sequences shown in FIG. 2C may also be used as replication origin sequences in the substrates of the present invention. When a subsequence of a replication origin box sequence is used, the subsequence preferably includes at least a 10 nucleotide and more preferably a 14 nucleotide subsequence of one of the replication origin box sequences shown in FIG. 2C. Mutant forms of the replication origin box sequences shown in FIG. 2C, or subsequences thereof, which have sufficient homology to preserve the helicase activity of the substrate may also be used in the substrate as the replication origin sequence and are intended to fall within the scope of the present invention.

Any of the substrates of the present invention may optionally further include one or more detectable markers. The detectable markers may be any marker which can be used to determine the presence or absence of the substrate or the first or second sequence of the substrate in a biological sample. The detectable marker may be attached to either the first or second sequence of the substrate. The detectable marker is preferably a dye which can be seen under natural light or with the assistance of an excitation light source to cause fluorescence. In a preferred embodiment, the detectable marker is a fluorescent dye. Examples of fluorescent dyes that may be used include, but are not limited to fluorescein and its derivatives, rhodamine and its derivatives, dansyl, umbeliferone, acridimium, and chemiluminescent molecules such as luciferin and 2,3-dihydrophthalazinediones. The fluorescent dye may also be an energy transfer fluorescent dye.

The detectable marker may also be a molecule which binds to an analytically detectable counterpart. For example, the detectable marker may be covalently attached to or incorporated into the substrate, for example, as taught by Ward, European Patent Application No. 63,879. In such instances, the substrate is detected by adding the analytically detectable counterpart which specifically binds to the substrate, thereby enabling detection of the substrate. Examples of such detectable markers and their analytically detectable counterparts include biotin and either fluorescent or chemiluminescent avidin. Antibodies that bind to an analytically detectable antigen may also be used as the detectable marker. The detectable marker may also be a molecule which, when subjected to chemical or enzymatic modification, becomes detectable such as those disclosed in Leary, et al., Proc. Natl. Acad. Sci. (U.S.A.), 80:4045–4049 (1983).

The substrate may also optionally be immobilized on a solid support. Depending on the application, either the first or second strand of the substrate may be immobilized on the solid support. One of the strands of the substrate may be synthesized onto the solid support using methodologies known in the art. Alternatively, linkers may optionally be used to attach the the substrate to the solid support. These linkers may have different lengths depending on the application.

Figure 3:
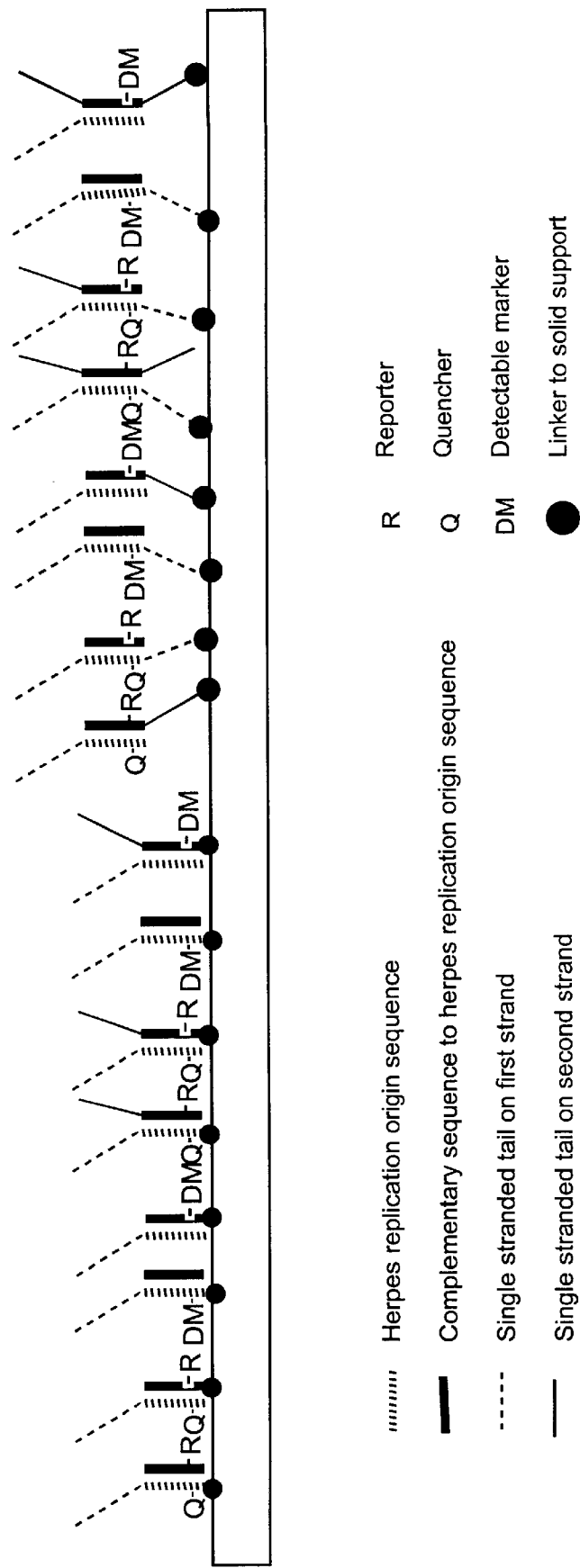
FIG. 3 illustrates different embodiments of substrates immobilized on a solid support.

FIG. 3 illustrates different embodiments of substrates immobilized on a solid support where either the first or second strand is attached (covalently or non-covalently) to the solid support. Different positionings of detectable markers (DM) on the substrates are also illustrated.

Examples of solid supports for immobilizing the substrates include, but are not limited to controlled pore glass, glass plates, polystyrene, avidin coated polystyrene beads, cellulose, nylon, acrylamide gel and activated dextran. CPG, glass plates and high cross-linked polystyrene. These solid supports are preferred for hybridization and diagnostic studies because of their chemical stability, ease of functionalization and well defined surface area.

Immobilization on the solid support may be via a covalent attachment. For example, a wide variety of linkers are known in the art for covalently attaching nucleic acid sequences to a solid support and may be used in the present invention.

Alternatively, immobilization on the solid support may be via a non-covalent attachment using a pair of complexing agents. The complexing agents used to attach the substrate to the solid support may be any pair of complexing agents which form a strong binding pair. Examples of suitable binding pairs of complexing agents include, but are not limited to antibody-antigen pairs, biotin-avidin and digoxigenin-anti-digoxigenin. Avidin-biotin and analogues and derivatives thereof are particularly preferred as binding pairs due to their enhanced thermal stability. Examples of avidin derivatives include, but are not limited to, streptavidin, succinyl avidin, ferritin avidin, enzyme avidin and cross-linked avidin. Examples of biotin derivatives include, but are not limited to caproylamidobiotin and biocytin. Examples of biotin analogues include, but are not limited to desthiobiotin and biotin sulfone. Biotin-antibiotin antibody is an example of a suitable antibody-antigen pair.

The present invention relates to a series of assays which utilize the ability of the substrates of the present invention to selectively detect helicase activity in the UL9 protein. As will be discussed herein, the assays of the present invention have a variety of useful applications including detecting UL9 helicase activity, detecting an ability of a chemical entity to inhibit UL9 helicase activity, and the detection of herpes infected samples. By using substrates immobilized on a solid support, the methods can be readily adapted for a high throughput assay for anti-herpes drugs.

According to one embodiment of the invention, a method is provided for detecting UL9 helicase activity in a sample. The method includes contacting the sample with a substrate according to the present invention, ATP and ICP8; and detecting unwinding of the substrate, unwinding of the substrate indicating the presence of UL9 helicase activity.

Detection of unwinding of the substrate may be performed by attaching a detectable marker to the substrate and detecting a change in the concentration of detectable marker due to the unwinding of the substrate.

Detection of unwinding of the substrate may also be performed by gel electrophoresis to detect the presence of single strands of the substrate.

According to this variation, after the sample is contacted with the substrate and ICP8, the reaction mixture containing the sample and substrate is subjected to electrophoresis and the presence of one or both of the single strands of the substrate is detected.

Gel-based helicase assays have several major disadvantages. Gel assays generally include radiolabeled substrates and extensive gel purification to obtain substrates of high quality. The purity of the UL9 substrate is important for detecting helicase activity since small amounts of contaminated ssDNA oligonucleotides can interact with ICP8, resulting in no helicase activity. The detection of the helicase assay requires autoradiography and the ssDNA products are quantitated by a PhosphoImager.

Detection of unwinding of the substrate may be performed by attaching a UL9 substrate to a solid support. By contrast to gel-based helicase assays, helicase assays where the UL9 substrate is immobilized on a solid support (solid phase assay) allows for improved purification of the UL9 substrate prior to the assay as well as the mass production of the helicase substrate for high throughput screening.

Figure 4:
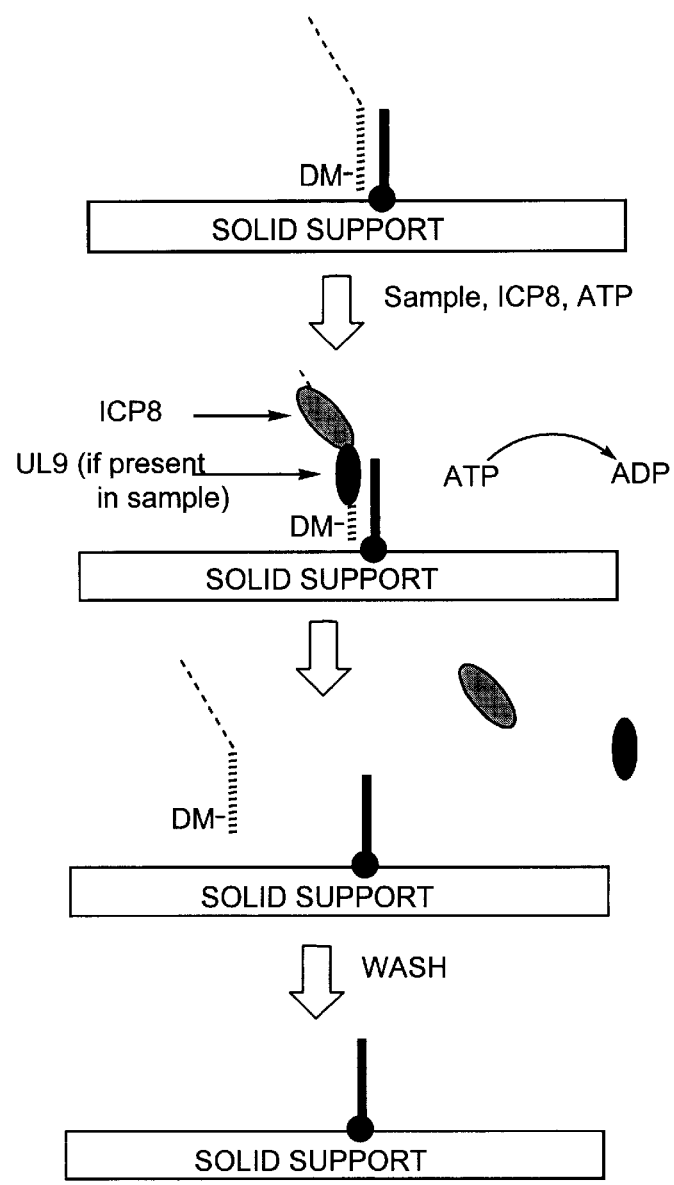
FIG. 4 illustrates a solid phase assay for detecting UL9 helicase activity.

In one embodiment, illustrated in FIG. 4, the substrate is attached to a solid support and a detectable marker is attached to a strand of the substrate which is not attached to the solid support. The substrate attached to the solid support is then contacted with the sample, ATP and ICP8. Afterward, the solid support is washed. If the substrate is unwound by UL9 in the sample, the detectable marker can be removed by the washing, yielding less detectable marker attached to the solid support.

Figure 5:
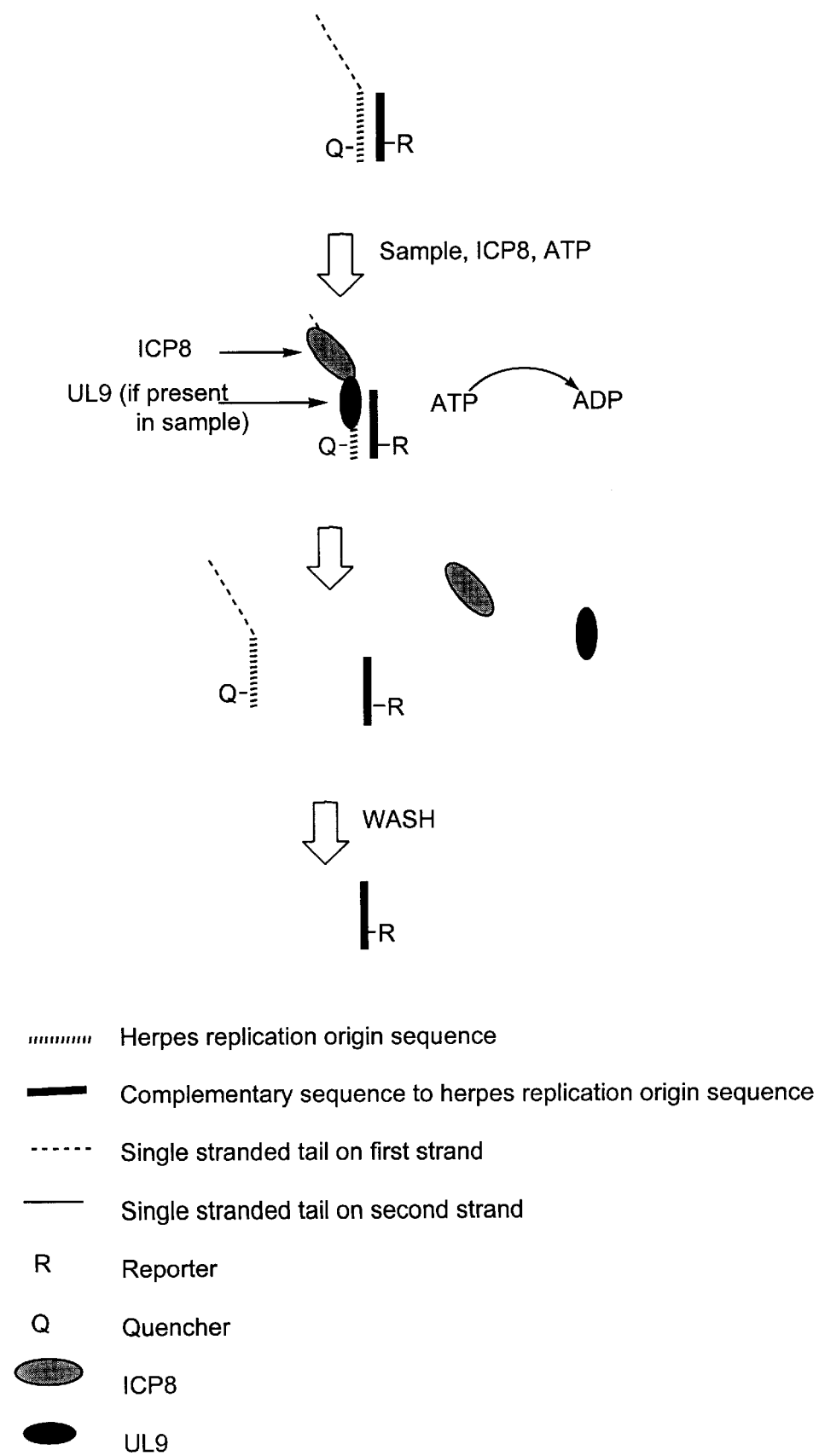
FIG. 5 illustrates an assay for detecting UL9 helicase activity where the substrate includes a reporter—quencher pair.

In another embodiment, illustrated in FIG. 5, a fluorescent reporter molecule is attached to one of the strands of the substrate and a quencher molecule which quenches the fluorescence of the reporter molecule is attached to the other strand of the substrate. The substrate is then contacted with the sample, ATP and ICP8. If the substrate is unwound by UL9 in the sample, the strand with the quencher molecule is no longer hybridized to the strand with the reporter molecule. As a result, the quencher is no longer within quenching distance of the reporter molecule and the fluorescence of the sample increases.

Figure 6:
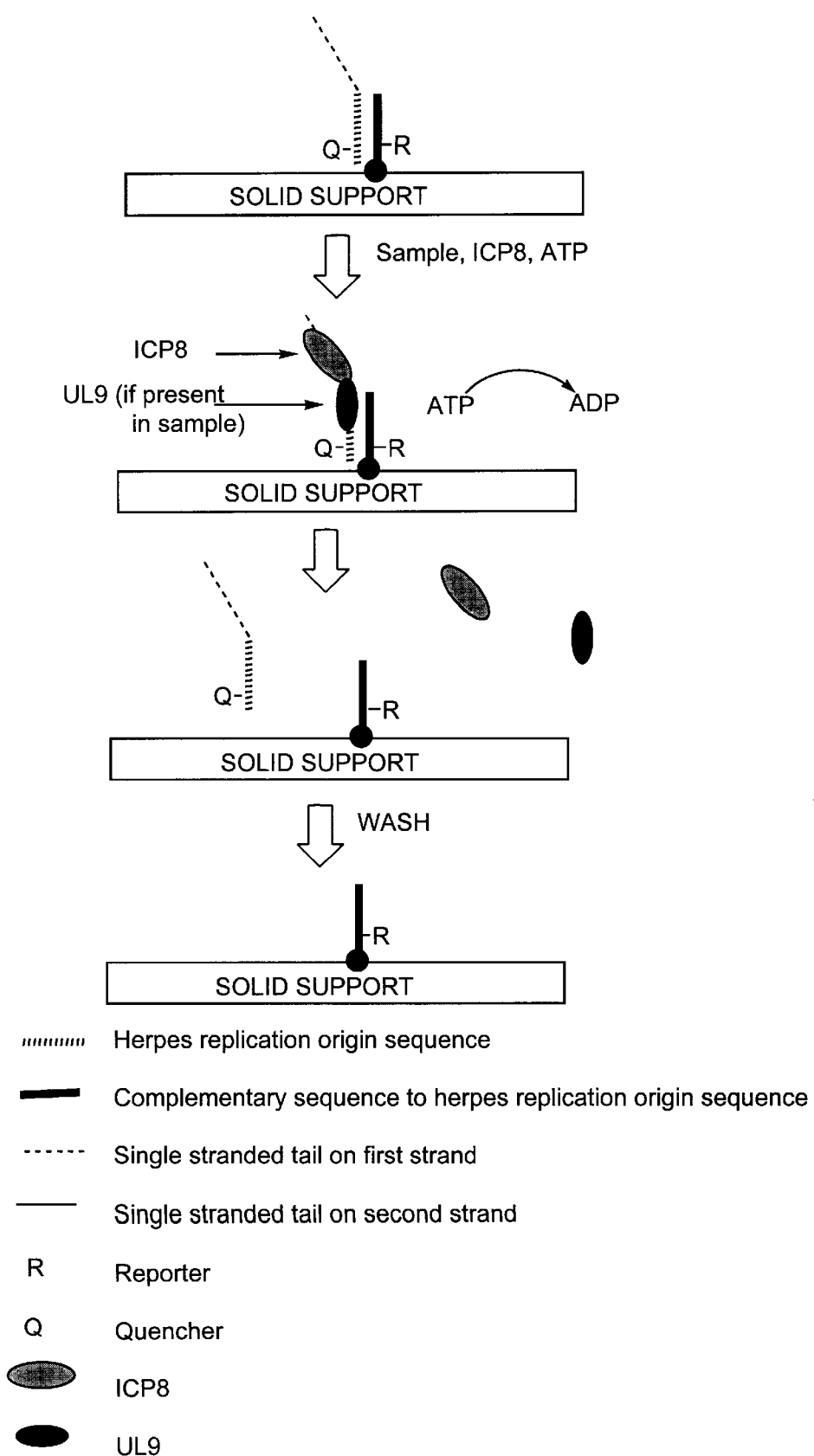
FIG. 6 illustrates a solid phase assay for detecting UL9 helicase activity where the substrate includes a reporter—quencher pair.

In a variation of the above embodiment, illustrated in FIG. 6, the substrate is attached to a solid support. A fluorescent reporter molecule is attached to one of the strands of the substrate and a quencher molecule which quenches the fluorescence of the reporter molecule is attached to the other strand of the substrate. The substrate is then contacted with the sample and ICP8. If the substrate is unwound by UL9 in the sample, the strand with the quencher molecule is no longer hybridized to the strand with the reporter molecule. As a result, the quencher is no longer within quenching distance of the reporter molecule and the fluorescence of the sample increases. The above method may optionally include a washing step to remove the strand of the substrate which is unwound and not attached to the solid support. Although the reporter molecule is illustrated in the figure as being attached to the strand of the substrate which is attached to the solid support, it is noted that the reporter molecule may be attached to the strand of the substrate which is not attached to the solid support.

As evident in many biological systems, an origin unwinding step is a highly regulated event, and the enzymes involved are believed to be ideal drug targets. Specific inhibition of origin unwinding by an anti-viral compound would prevent further DNA replication carried out by DNA polymerases and other essential replication factors. Accordingly, an important aspect of the present invention is the utilization of the substrates according to the present invention to screen different chemical entities for their ability to inhibit UL9 helicase activity.

A chemical entity may be screened according to the present invention for an ability to inhibit UL9 helicase activity by contacting the combination of the UL9 protein, ATP, ICP8 and a substrate according to the present invention with the chemical entity. Helicase activity of the UL9 protein is then determined based on an unwinding of the UL9 substrate. According to this method, a degree of unwinding of the substrate can be detected at a selected period of time. Alternatively, the degree of unwinding of the substrate can be detected at a series of times or continuously in order to determine the effect the chemical entity has on the rate of unwinding by the UL9 protein. Unwinding of a substrate by the UL9 protein can be detected by the various methods known in the art as well as the methods for detecting UL9 helicase activity taught in this application. In one particularly preferred embodiment, the substrate is immobilized on a solid support. Detection of unwinding of the immobilized substrate may be detected, for example, by the schemes illustrated in FIGS. 4 and 6.

Immobilized UL9 substrates can also be used for detecting the presence of HSV in a sample. In the presence of non-specific competitor DNA, the UL9 protein and ICP8 can specifically bind to a UL9 substrate. The UL9 protein and ICP8 bound to the UL9 substrate can then be detected by antibodies directed against the UL9 protein and ICP8.

In one embodiment, a sample, preferably a cell lysate, is contacted with UL9 substrates according to the present invention. The complex of the UL9 protein and ICP8 bound to the UL9 substrate is then detected. In one variation of the embodiment, the UL9 substrate is immobilized on a solid support. The immobilized UL9 substrate is then contacted with a sample. After a period of incubation, the solid support is washed to remove any UL9 protein and ICP8 which is not bound to the substrate. The complex of the UL9 protein and ICP8 bound to the immobilized UL9 substrate is then detected. This method serves as an excellent tool for screening for actively replicating herpes-infected samples, distinct from other screening assays which utilize anti-herpes surface proteins.

EXAMPLES

1. Preparation of UL9 substrates.

Table 1 provides a series of sequences which were used to form the different UL9 substrates described in the following examples. The different substrates formed are illustrated in FIG. 7.

To prepare UL9 substrates of the present invention, the oligonucleotides appearing in Table 1 were purified by 16% polyacrylamide gel electrophoresis under denaturing conditions.

TABLE 1

| SEQ. I.D. No. | SEQUENCE |
|---|---|
| 1 | CATGCTCGCAGCGGGACGAAGTGCGAACGCTTGCG |
| 2 | CGCGAAGCGTTCGCACTTCGTCCCGCCTTCCTGCGCCTTCCTGT |
| 3 | CATGCTCGCAGCGGGACGACACCTACGAGCGCCCG |
| 4 | CGGGGCGCTCGTAGGTGTCGTCCCGCCTTCCTGCGCCTTCCTGT |
| 5 | GCGGGACGAAGTGCGAACGCTTCGCG |
| 6 | CGCGAAGCGTTCGCACTTCGTCCCGC |
| 7 | CATGCTCGCACGTCCTTCGCGGGACGAAGTGCGAACGCTTCGCG |
| 8 | CATGCTCGCACGCGAAGCGTTCGCACTTCGTCCCGC |
| 9 | GCGGGACGAAGTGCGAACGCTTCGCGCTTCCTGCGCCTTCCTGT |
| 10 | CGCGAAGCGTTCGCACTTCGTCCCGC |
| 11 | CGCGAAGCGTTCGCACTTCGTCCCGCCTTC |
| 12 | CGCGAAGCGTTCGCACTTCGTCCCGCCTTCCTGC |

Bands corresponding to the full-length oligonucleotides were excised and gently homogenized in elution buffer (10 mM Tris-HCl, pH 7.8, 0.5 M ammonium acetate, 1 mM EDTA, 0.1% SDS) and eluted at room temperature overnight. The homogenates were briefly centrifuged in a 0.4 $\mu$m filter unit to remove the gel, and the oligonucleotides were precipitated with ethanol.

One of the strands to be used in the substrate was generally 5' end-labeled with T4 polynucleotide kinase and [$\gamma$-$^{32}$P]ATP. After the reaction, free radioactive ATP was removed through Bio-Spin 6 column. The radiolabeled strand was then mixed with a 5-fold excess of a complementary strand in 50 mM Tris-HCl, pH 7.5 and 200 mM NaCl. The oligonucleotides were then incubated at 90° C. for 15 min, at 65° C. for 10 min, and at room temperature for at least 3 hour. The duplex oligonucleotides were electrophoresed through a 15% native polyacrylamide gel in 1×TBE (45.5 mM Tris base/44.5 mM boric acid/1 mM EDTA) at 10 volts/cm. Bands corresponding to a UL9 substrate were excised from the gel and eluted as described above. The purity of the substrates was critical since free ssDNA or excess salt inhibits helicase activity.

UL9 substrates with 3' and 5' single-stranded tails (Substrate I) were prepared by annealing the 5' end-labeled 44-mer (SEQ ID. No. 2) with the 36-mer (SEQ ID. No. 1). UL9 substrates with only a 3' single-stranded tail (Substrate II) were prepared by annealing the 5' end-labeled 26-mer (SEQ ID. No. 5) with the wild-type 44-mer (SEQ. ID. No. 2). UL9 substrates (Substrate III) ssDNA tails in the opposite orientation were prepared by annealing the 5' end-labeled 36-mer (SEQ ID. No 8) with the 44-mer (SEQ ID. No. 9). UL9 substrates with only a 5' single-stranded tail (Substrate IV) were prepared by annealing the 5' end-labeled 26-mer (SEQ ID. No. 6) with the 44-mer (SEQ ID. No. 7). UL9 substrates with differing lengths of 3' ssDNA tails (Substrate V; Substrate VI; Substrate VII; Substrate I) were prepared by annealing the 5' end-labeled 26-mer (SEQ ID. No. 10), 30-mer (SEQ ID. No. 11), 34-mer (SEQ ID. No 12), or 44-mer (SEQ ID. No. 2) with the wild-type 36-mer (SEQ ID. No. 1).

2. Enzyme purification.

Recombinant UL9 protein was purified from nuclear extracts of UL9 baculovirus-infected Sf21 insect cells. Briefly, purification steps consisted of S-Sepharose, Heparin Sepharose, Hydroxylapatite, and Mono-S chromatography. The purification was monitored by a gel mobility shift assay using $^{32}$P-labeled UL9 substrate, DNA-dependent ATPase, and Western blot analysis with anti-UL9 antibodies. The purified UL9 protein consisted of a single polypeptide that migrated with a molecular mass of 83 kDa, following SDS-PAGE and silver staining and contained 3'-5' helicase, DNA-dependent ATPase, and $ori_S$ binding activities. Recombinant ICP8 was overexpressed in a baculovirus expression system. Cytosolic fractions of Sf21 insect cells were chromatographed on DEAE-Sepharose, phosphocellulose, and heparin Sepharose. The purified ICP8 migrated as a single polypeptide with a molecular mass of 120 kDa, following SDS-PAGE and silver staining. It reacted with anti-ICP8 antibodies, and contained no detectable helicase, nuclease, or ATPase activity.

3. DNA unwinding assay.

To measure unwinding of a UL9 substrate, reaction mixtures (25 µl) containing 50 mM Hepes-KOH, pH 7.8, 100 mM NaCl, 5 mM dithiothreitol, 10% glycerol, 10 µg of bovine serum albumin, 0.2–2 pmol of UL9 substrate, 2 pmol of UL9 protein, and different amounts of ICP8 were assembled on ice. ATP (4 mM) was added to the reaction mixtures, which were then incubated at 37° C. for 60 min. The reactions were stopped by the addition of 6.5 µl of stop solution (100 mM EDTA, 1% SDS, 20 µg of proteinase K), and the mixtures were incubated for an additional 10 min at 37° C., followed by electrophoresis through a 15% polyacrylamide gel at 10 volts/cm. The gel was then dried on Whatman DE81, and quantitated with a PhosphoImager (Molecular Dynamics).

4. UL9 protein binds to substrate with fully duplex herpes replcation origin but fails to unwind it.

Failure to detect unwinding of $ori_S$ by the UL9 protein promoted closer examination of the interaction of the UL9 protein with the high affinity Box I sequence alone. The Box I sequence is present in both $ori_S$ and $ori_L$ and consists of 18 nucleotide residues, including the core binding site for the UL9 protein. Previous DNase I footprinting and gel shift results showed that a homodimer of UL9 protein binds to the Box I (ka=0.3 nM). A $^{32}$P-labeled, fully duplex Box I sequence was incubated with stoichiometric amounts of UL9 protein and ATP in the presence or absence of ICP8. Although hydrolysis of the ATP was observed, the UL9 protein was unable to unwind a duplex containing the Box I sequence.

5. UL9 protein binds to substrate with single stranded tail but fails to unwind it in the absence of ICP8.

Modified substrates were synthesized to which ssDNA strands were formed downstream of the Box I sequence. The location of these ssDNA strands was intended to mimic the easily unwound A/T-rich sequence that links Boxes I and II, as illustrated in FIG. 2A. Binding of the UL9 protein to Box I to which ssDNA tails are attached was verified by gel mobility shift analysis. Despite the presence of the ssDNA tails, unwinding of Box I by the UL9 protein alone could not be detected.

6. UL9 protein unwinds substrate with single stranded tail in the presence of ICP8.

Applicant theorized that ICP8 might influence UL9 helicase activity when bound to a substrate containing a herpes replication origin. In order to access whether ICP8 influences unwinding of a UL9 substrate by the UL9 protein, different amounts of ICP8 were incubated with the UL9 protein (2 pmol) and ATP for 60 min at 37° C. Substrate I (SEQ ID. No.: 30) as illustrated in FIG. 7 was used in this example.

Figure 8:
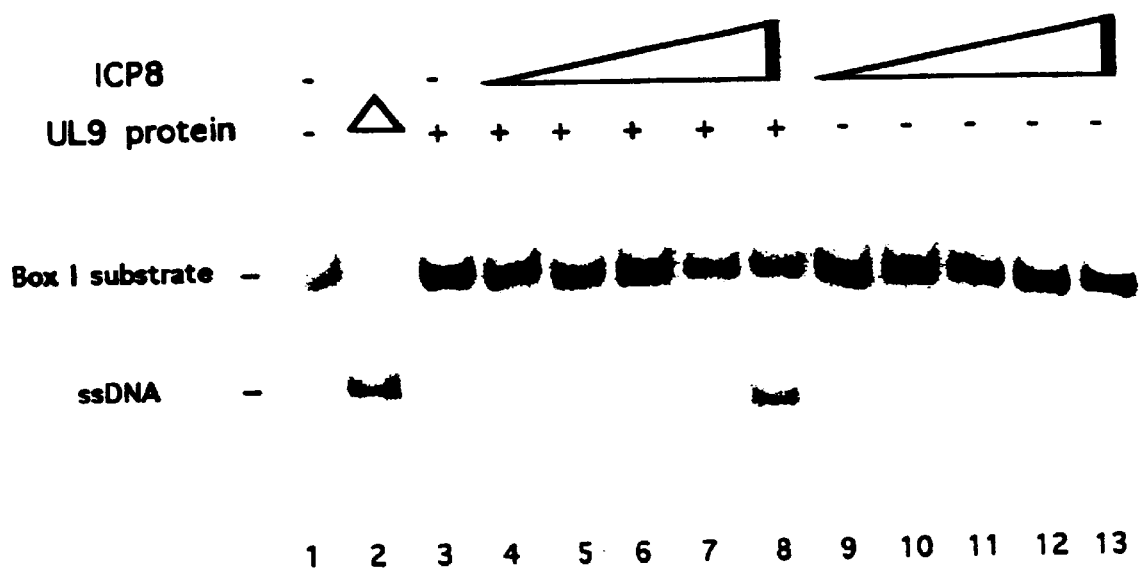
FIG. 8 is a gel illustrating the helicase activity of a UL9 substrate by the UL9 protein at different concentrations of ICP8.

FIG. 8 is a gel illustrating the helicase activity of the UL9 substrate by the UL9 protein at different concentrations of ICP8. In lane 1, no UL9 protein was present and no helicase activity was observed. In lane 2, the UL9 substrate was boiled. As can be seen from the gel, the duplex formed from the first and second strands of the UL9 substrate was disrupted and the first and second strands rendered single stranded.

In lanes 3–8, 0; 0.001; 0.01; 0.1; 1; and 10 pmol of ICP8 were introduced with the UL9 protein (2 pmol). As illustrated in FIG. 8, a small amount of helicase activity by the UL9 substrate was observed when the UL9 protein (2 pmol) was used in combination with 1 pmol of ICP8 (Lane 7). A significantly greater amount of helicase activity by the UL9 substrate was observed when the UL9 protein (2 pmol) was used in combination with 10 pmol of ICP8 (Lane 8). In view of the data presented in FIG. 8, UL9 protein helicase activity was shown to be dependent on the presence of ICP8. ICP8 is preferably present in at least stoichiometric amounts.

In lanes 9–13, 0.001; 0.01; 0.1; 1; and 10 pmol of ICP8 were used in the absence of the UL9 protein. No unwinding of the substrate was observed. It is interesting to note that no unwinding was detected with ICP8 alone, which under certain conditions can display helix destabilizing activity. Boehmer and Lehman, J. Virol. 67, 711–715 (1993).

7. Mutation of replication origin in substrate to prevent specific binding of UL9 protein to substrate inhibited helicase activity.

Figure 9:
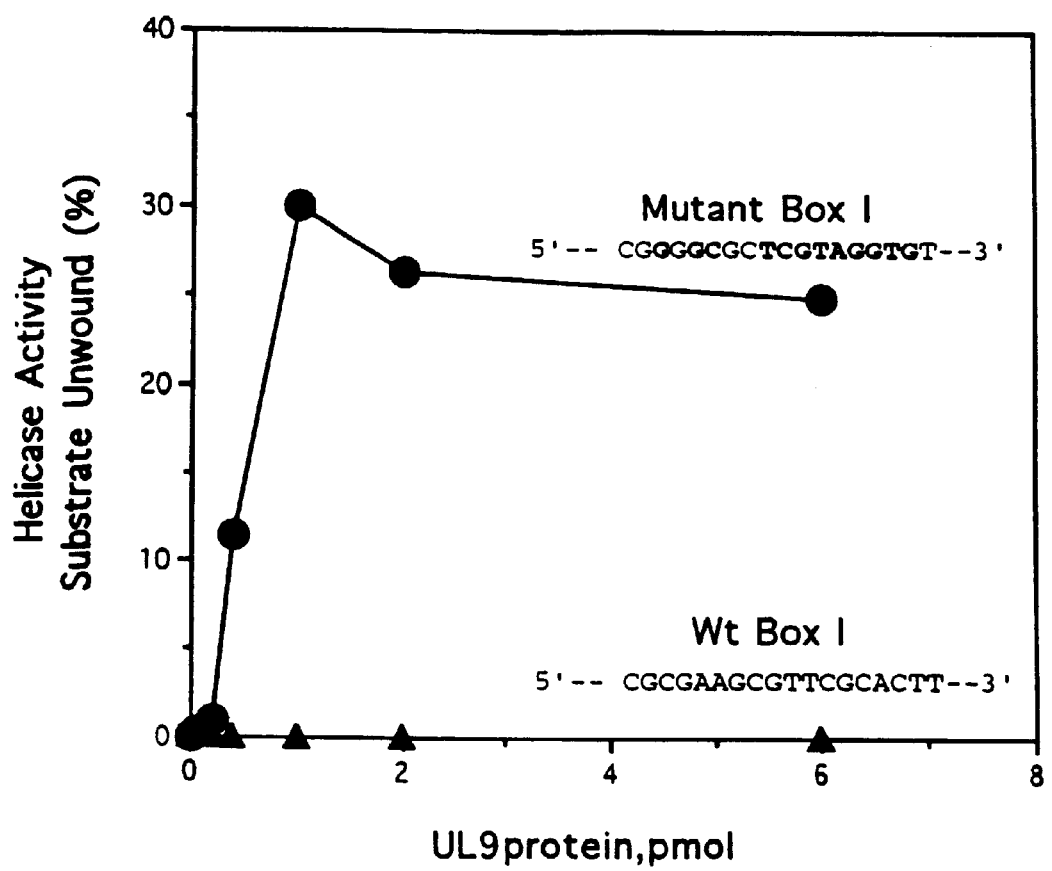
FIG. 9 compares the helicase activity of UL9 substrates containing the wild-type (Wt) and mutant Box I binding sequences.

FIG. 9 compares the helicase activity of UL9 substrates containing the wild-type (Wt) and mutant Box I binding sequences. Substrate I (SEQ ID. No.: 30) as illustrated in FIG. 7 was used in this example as the wild-type substrate. In the case of the Mutant Box I substrate, the core binding site for UL9 protein was mutated to prevent specific binding (mutations shown in boldface type) Hazuda et al., J. Biol. Chem. 267,14309–14315 (1992).

Increasing amounts of the UL9 protein (as indicated) were incubated with the UL9 substrates (2 pmol) for 60 min at 37° C. The reaction mixtures were electrophoresed through a 15% polyacrylamide gel, and the ssDNA products of the reaction were quantitated with a PhosphorImager.

Although the UL9 protein alone was unable to unwind the UL9 substrate, mutation of the Box I sequence to prevent binding of the UL9 protein resulted in significant unwinding. The ability of the UL9 protein to unwind the mutant duplex in the absence of ICP8 is a manifestation of the nonspecific helicase activity associated with the UL9 protein, which requires the loading site provided by the attached 3' single strand.

8. C-Terminal portion of UL9 protein required for unwinding.

Figure 10:
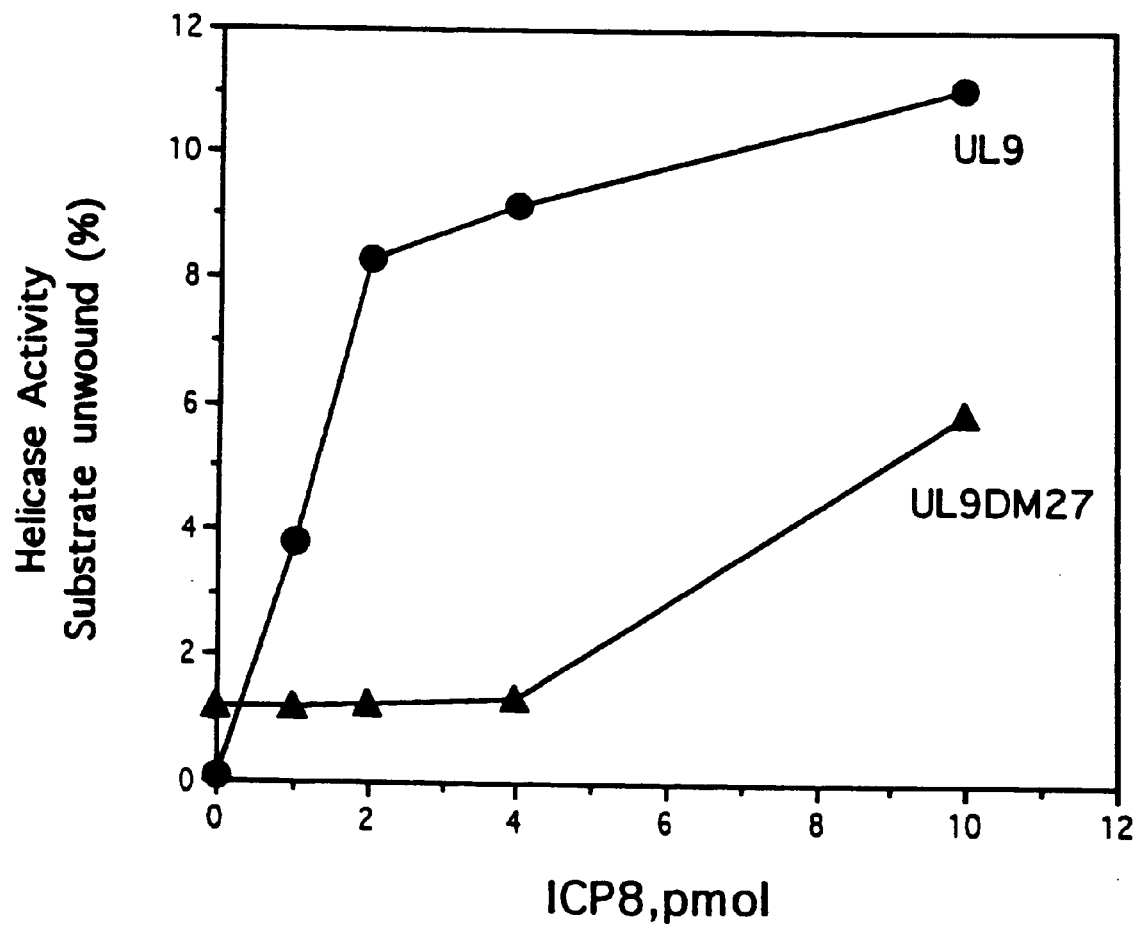
FIG. 10 illustrates a plot of helicase activity versus ICP8 concentration for wild-type UL9 protein and mutant UL9 protein (UL9DM27).

FIG. 10 illustrates the importance of the C-terminal portion of UL9 protein to unwind the UL9 substrate in the presence of ICP8. A mutant UL9 protein (UL9DM27) has been produced which lacks 27 amino acids at the C terminus and interacts only weakly with ICP8 in solution. Arbuckle and Stow, J. Gen Virol. 74, 1379–1355 (1993); Boehmer and Lehman, J. Biol. Chem, 269, 29329–29334 (1994). The mutant protein binds $ori_S$ normally and exhibits helicase and DNA-dependent ATPase activities. However, the deletion of the C-terminal portion resulted in no replication of HSV-1 DNA in vivo.

The wild-type UL9 protein and mutant UL9 protein (UL9DM27) (2 pmol) were each incubated with increasing amounts of ICP8 and UL9 substrate (2 pmol) for 60 min at 37° C. Substrate I (SEQ ID. No.: 30) as illustrated in FIG. 7 was used in this example. Following 15% PAGE, the ssDNA products of the reaction were quantitated with a PhosphoImager.

FIG. 10 illustrates a plot of helicase activity versus ICP8 concentration for wild-type UL9 protein and mutant UL9 protein (UL9DM27). As can be seen from the figure, helicase activity in the UL9DM27 mutant was significantly reduced as compared to UL9 helicase activity at comparable concentration levels. This finding suggests that an interaction between the C-terminal portion of the UL9 protein and ICP8 is needed to promote the unwinding of Box I. In contrast to the wild-type UL9 protein, the mutant protein showed a low level of helicase activity in the absence of ICP8. This effect may be related to its high intrinsic helicase activity. These findings demonstrate that a specific complex of UL9 protein and ICP8 can unwind Box I to which ssDNA is attached.

The fact that a fully duplexed UL9 substrate (e.g., without single stranded tails) was not unwound by the UL9 protein-ICP8 complex suggests that the unwinding of a UL9 substrate is mediated by a complex consisting of the UL9 protein and ICP8 bound to the ssDNA. Thus, in contrast to SV40 large T antigen, where unwinding of the origin requires an SSB solely to maintain the separation of the single strands produced by its helicase action, an essentially passive role, ICP8 appears to be an active participant in the unwinding process.

9. Comparison of the effect of different single stranded tails on UL9 helicase activity.

A major difference between the fully duplexed Box I substrates used in previous experiments and the UL9 substrates of the present invention is the addition of the ssDNA tails either downstream or upstream of the herpes replication origin sequence. In order to investigate further the role of the single strands on the unwinding of the substrate, a series of substrates differing only in the length and orientation of their single-stranded tails were synthesized and examined for their ability to be unwound by the UL9 protein-ICP8 complex.

Figure 11A:
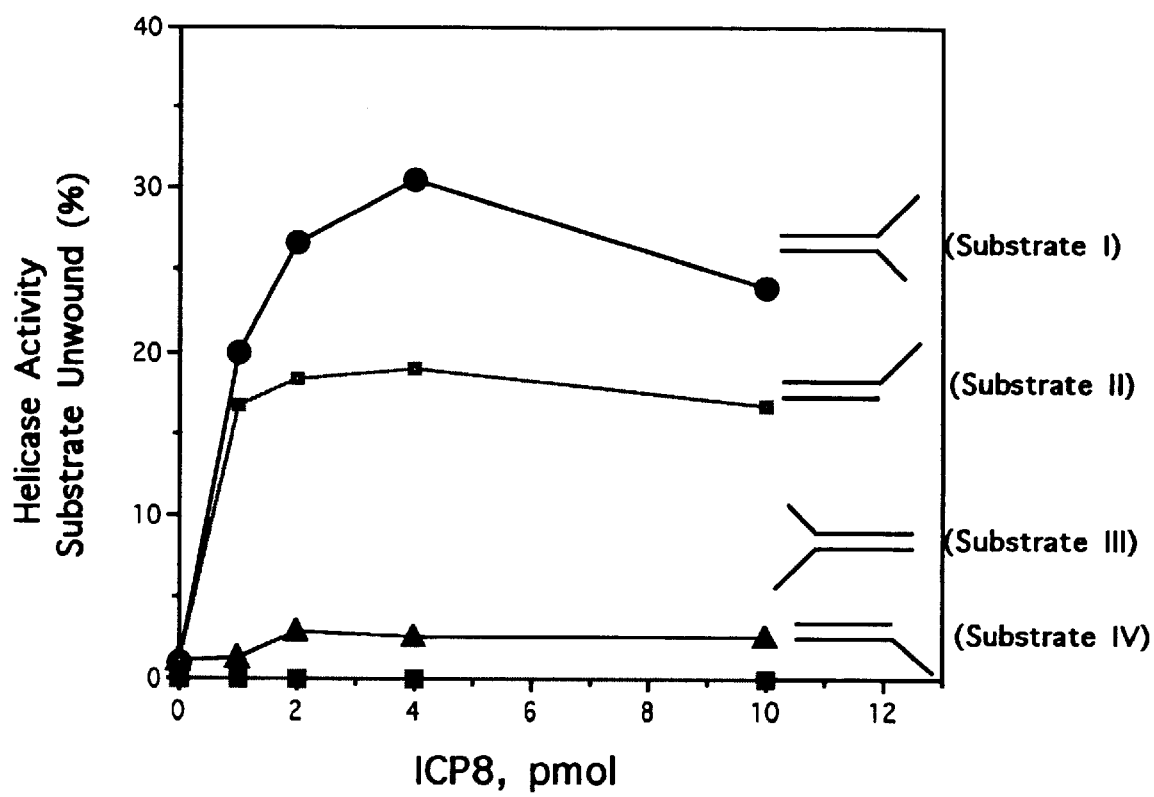
FIG. 11A illustrates the effect of different single stranded tails on the unwinding activity of a UL9 substrate.

FIG. 11A illustrates the effect of different single stranded tails on the unwinding activity of a UL9 substrate. In the figure, (I) is a UL9 substrate with 3' and 5' ssDNA tails (Substrate I; SEQ ID. No.: 30); (II) is a UL9 substrate with a 18-nt 3' ssDNA tail (Substrate II; SEQ ID. No.: 31); (III) is a UL9 substrate with ssDNA tails in the opposite orientation (Substrate III; SEQ ID. No.: 32); and (IV) is a UL9 substrate with a 18-nt 5' ssDNA tail (Substrate IV; SEQ ID. No.: 33).

With regard to each of the substrates, the UL9 protein (2 pmol) was incubated with the respective UL9 substrate, and the indicated amounts of ICP8 at 37° C. for 60 min. Following 15% PAGE, the ssDNA products were quantitated with a PhosphoImager.

As can be seen from the figure, a tail on the first sequence (top sequence), either 5' (III) or 3' (I), (II) appears to be critical to a UL9 substrate exhibiting helicase activity. A 3' tail on the first sequence appears to enhance the level of helicase activity. A 5' tail on the second sequence in combination with a 3' tail on the first sequence appears to further enhance the level of helicase activity. Optimal unwinding was observed at a stoichiometry of 1 mol of ICP8 per mol of 3' ssDNA tail. The UL9 protein alone was unable to unwind any of the substrates in the absence of ICP8.

10. Comparison of the effect of different length single stranded tails on UL9 helicase activity.

Figure 11B:
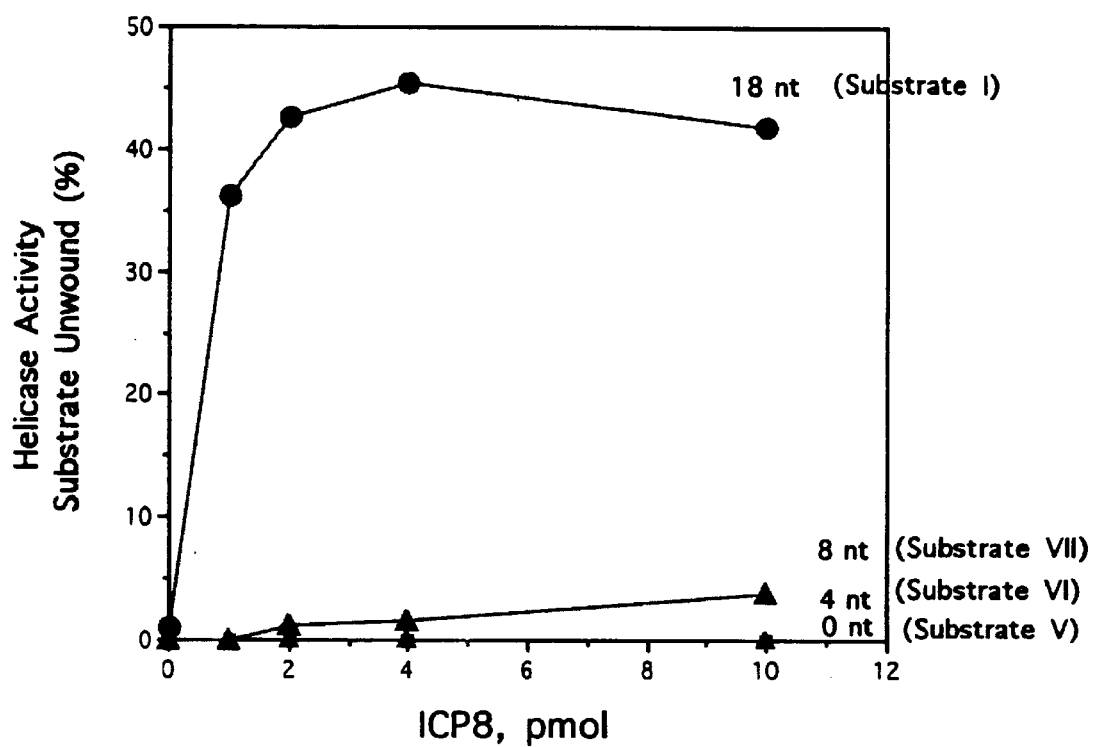
FIG. 11B illustrates the effect of different tail lengths on the unwinding activity of a UL9 substrate.

The effect of different length 3' ssDNA tails was also examined. FIG. 11B illustrates the effect of different tail lengths on the unwinding activity of a UL9 substrate. UL9 substrates having a 3' tail and a 5' tail as in (I) of FIG. 11A were used where the length of the 3' tail was varied between 0 nt, 4 nt, 8 nt, and 18 nt. The UL9 substrates used in this example correspond to Substrates V (SEQ. ID No. 34), VI (SEQ. ID No. 35), VII (SEQ. ID No. 36), I (SEQ. ID No. 30), respectively.

The UL9 protein (2 pmol) was incubated with the respective UL9 substrate, and the indicated amounts of ICP8 at 37° C. for 60 min. Following 15% PAGE, the ssDNA products were quantitated with a PhosphoImager.

As can be seen from the figure, a 3' tail of 8 nt exhibited helicase activity whereas a 3' tail of 4 nt did not exhibit helicase activity. A 3' tail 18 nt in length exhibited significantly greater helicase activity than an 8 nt 3' tail. Estimates of the binding site size of ICP8 for ssDNA range from 12 to 18 nt, suggesting that binding of at least one ICP8 monomer to the ssDNA tail is required to form an active complex with the UL9 protein.

11. High throughput assay for anti-UL9 helicase compounds.

This example describes a solid phase helicase assay using a UL9 substrate according to the present invention. The solid phase helicase assay provides for the rapid screening for anti-herpes drugs and is adaptable for use as a high throughput assay.

A first step in the solid phase helicase assay is the immobilization of only one strand of the UL9 substrate to the solid support. As illustrated in FIG. 12, a 5' biotinylated 44-mer is mixed with a 10-fold excess amount of the 36-mer and then heat-denatured, and annealed. The resulting duplex substrates and excess 36-mer are then applied onto streptavidin-coated 96 well plates or similar devices. Unbound ssDNA 36-mer is removed, and the UL9 protein and ICP8 are added. The helicase reaction is initiated by adding ATP. As the UL9-ICP8 complex unwinds the substrate in an ATP-dependent manner, the complimentary strand (36-mer) which is not immobilized on a solid phase, will become dissociated from the duplex. During washing, free ssDNA products are removed. The unwound UL9 substrate containing the 36-mer is then quantitated.

The method for detecting helicase activity can be varied, depending upon the nature of the detectable marker or markers attached to the strands of the UL9 substrate. As shown in FIG. 12, a dual reporter system can be used to monitor the helicase activity. The immobilized UL9 substrate can be verified by quantitating the amount of reporter A, while the ssDNA products can be continuously measured as the UL9-ICP8 complex unwinds the substrate.

Alternatively, a UL9 substrate with a digoxigenin-labeled 36 mer attached to the solid support can be used. Digoxigenin can be detected with anti-digoxigenin antibody. The antibodies bound to the digoxigenin-labeled 36-mer can be detected with HRPsubstrates at 450 nm.

Figure 13:
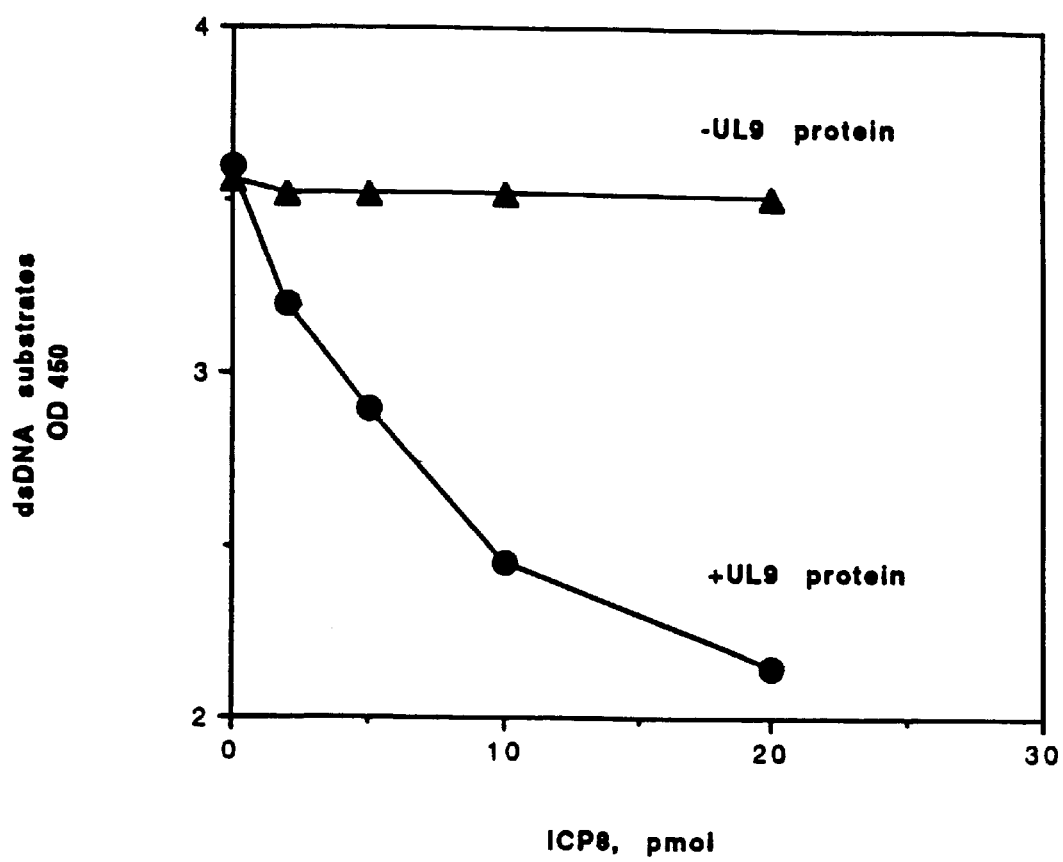
FIG. 13 illustrates unwinding of an immobilized UL9 substrate by the UL9 protein and ICP8.

FIG. 13 shows a graph representing the amount of digoxigenin remaining after incubation with 2 pmol of UL9 and different amounts of ICP8. As illustrated, the amount of digoxigenin remaining decreases as the amount of ICP8 increases.

12. Detection of the UL9 activity in HSV-infected samples.

Immobilized UL9 substrates can be used for detecting the UL9 protein and ICP8 from HSV-infected cell lysates. In the presence of non-specific competitor DNA, the UL9 protein and ICP8 can specifically bind to a UL9 substrate immobilized on a solid phase. The UL9 and ICP8 bound to the UL9 substrate are then detected by antibodies directed against UL9 and ICP8. This method serves as an excellent tool for screening for actively replicating herpes-infected samples, distinct from other screening assays which utilize anti-herpes surface proteins.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A UL9 substrate comprising:
   a first strand including a UL9 herpes replication origin sequence and a first single stranded tail 3' relative to the herpes replication origin sequence; and
   a second strand including a sequence complementary to the UL9 herpes replication origin sequence.

2. The UL9 substrate according to claim 1 wherein the first single stranded tail is at least 8 nucleotides in length.

3. The UL9 substrate according to claim 1 wherein the first single stranded tail is between 8 and 100 nucleotides in length.

4. The UL9 substrate according to claim 1 wherein the first strand is a plasmid.

5. The UL9 substrate according to claim 1 wherein the replication origin sequence is selected from the group consisting of SEQ. ID Nos. 13–29, and at least 10 nucleotide long subsequences of SEQ. ID Nos. 13–29.

6. The UL9 substrate according to claim 1 wherein the first strand further includes a second single stranded tail 5' relative to the herpes replication origin sequence.

7. The UL9 substrate according to claim 6 wherein the second single stranded tail is at least 8 nucleotides in length.

8. The UL9 substrate according to claim 6 wherein the second single stranded tail is between 8 and 100 nucleotides in length.

9. The UL9 substrate according to claim 1 wherein the second strand further includes a single stranded tail.

10. The UL9 substrate according to claim 9 wherein the single stranded tail on the second strand is 5' relative to the sequence complementary to the herpes replication origin sequence.

11. The UL9 substrate according to claim 9 wherein the single stranded tail on the second strand is 3' relative to the sequence complementary to the herpes replication origin sequence.

12. A UL9 substrate comprising:
   a first strand including a UL9 herpes replication origin sequence and a first single stranded tail 3' relative to the herpes replication origin sequence;
   a second strand including a sequence complementary to the UL9 herpes replication origin sequence; and
   at least one detectable marker attached to at least one of the first and second strands.

13. The UL9 substrate according to claim 12 wherein the at least one detectable marker is attached to the first strand.

14. The UL9 substrate according to claim 12 wherein the at least one detectable marker is attached to the second strand.

15. The UL9 substrate according to claim 12 wherein at least one detectable marker is a fluorescent dye.

16. The UL9 substrate according to claim 12 wherein at least one detectable marker is a radiolabel.

17. The UL9 substrate according to claim 12 wherein the at least one detectable marker includes a reporter dye attached to one strand and a quencher dye attached to another strand of the substrate.

18. The UL9 substrate according to claim 12 wherein the first strand further includes a second single stranded tail 5' relative to the herpes replication origin sequence.

19. The UL9 substrate according to claim 12 wherein the second strand further includes a single stranded tail.

20. The UL9 substrate according to claim 19 wherein the single stranded tail on the second strand is 5' relative to the sequence complementary to the herpes replication origin sequence.

21. The UL9 substrate according to claim 19 wherein the first single stranded tail is 3' relative to the herpes replication origin sequence.

22. An immobilized UL9 substrate comprising:
   a first strand including a UL9 herpes replication origin sequence and a first single stranded tail 3' relative to the herpes replication origin sequence;
   a second strand including a sequence complementary to the UL9 herpes replication origin sequence; and
   a solid support to which one of the first and second sequences is attached.

23. The immobilized UL9 substrate according to claim 22 wherein the first strand further includes a second single stranded tail 5' relative to the herpes replication origin sequence.

24. The immobilized UL9 substrate according to claim 22 wherein the second strand further includes a single stranded tail.

25. The immobilized UL9 substrate according to claim 24 wherein the single stranded tail on the second strand is 5' relative to the sequence complementary to the herpes replication origin sequence.

26. The immobilized UL9 substrate according to claim 24 wherein the single stranded tail on the second strand is 3' relative to the sequence complementary to the herpes replication origin sequence.

27. The immobilized UL9 substrate according to claim 22 wherein at least one detectable marker is attached to at least one of the first and second strands.

28. A UL9 substrate comprising:
   a first strand including a UL9 herpes replication origin sequence and a first single stranded tail 5' relative to the herpes replication origin sequence; and
   a second strand including a sequence complementary to the UL9 herpes replication origin sequence and a single stranded tail 3' relative to the sequence complementary to the herpes replication origin sequence.

29. The UL9 substrate according to claim 28 wherein the first single stranded tail is at least 8 nucleotides in length.

30. The UL9 substrate according to claim 28 wherein the first single stranded tail is between 8 and 1 00 nucleotides in length.

31. The UL9 substrate according to claim 28 wherein the first strand is a plasmid.

32. The UL9 substrate according to claim 28 wherein the replication origin sequence is selected from the group consisting of SEQ. ID Nos. 13–29, and at least 10 nucleotide long subsequences of SEQ. ID Nos. 13–29.

33. The UL9 substrate according to claim 28 wherein the substrate further includes at least one detectable marker attached to at least one of the first and second strands.

34. The UL9 substrate according to claim 33 wherein the at least one detectable marker is attached to the first strand.

35. The UL9 substrate according to claim 33 wherein the at least one detectable marker is attached to the second strand.

36. The UL9 substrate according to claim 33 wherein at least one detectable marker is a fluorescent dye.

37. The UL9 substrate according to claim 33 wherein at least one detectable marker is a radiolabel.

38. The UL9 substrate according to claim 33 wherein the at least one detectable marker includes a reporter dye attached to one strand and a quencher dye attached to another strand of the substrate.

39. An immobilized UL9 substrate comprising:
   a first strand including a UL9 herpes replication origin sequence and a first single stranded tail 5' relative to the herpes replication origin sequence; and
   a second strand including a sequence complementary to the UL9 herpes replication origin sequence and a single stranded tail 3' relative to the sequence complementary to the herpes replication origin sequence; and
   a solid support to which one of the first and second sequences is attached.

40. The UL9 substrate according to claim 39 wherein the immobilized substrate further includes at least one detectable marker attached to at least one of the first and second strands.

41. The UL9 substrate according to claim 40 wherein the at least one detectable marker is attached to the first strand.

42. The UL9 substrate according to claim 40 wherein the at least one detectable marker is attached to the second strand.

43. The UL9 substrate according to claim 40 wherein at least one detectable marker is a fluorescent dye.

44. The UL9 substrate according to claim 40 wherein at least one detectable marker is a radiolabel.

45. The UL9 substrate according to claim 40 wherein the at least one detectable marker includes a reporter dye attached to one strand and a quencher dye attached to another strand of the substrate.

* * * * *

UNITED STATES PATENT AND TRADEMARK OFFICE
CERTIFICATE OF CORRECTION

PATENT NO.: 6,096,502

DATED: August 1, 2000

INVENTOR: Lee

It is certified that error appears in the above-identified patent and that said Letters Patent is hereby corrected as shown below:

Page 1, under [73] Assignee: delete "Bothwell, Wash." and insert:

--Bothell, Wash.--.

Page 1, under "Attorney, Agent, or Firm" after David J. Weitz" delete:

"Wilson Sonswi Goodrich & Rosati" and insert:

--Wilson Sonsini Goodrich & Rosati--.

Signed and Sealed this

Seventeenth Day of April, 2001

*Attest:*

NICHOLAS P. GODICI

*Attesting Officer*       *Acting Director of the United States Patent and Trademark Office*